US010688134B2

(12) United States Patent
Itescu et al.

(10) Patent No.: US 10,688,134 B2
(45) Date of Patent: *Jun. 23, 2020

(54) METHODS OF TREATING OR PREVENTING RESPIRATORY CONDITIONS

(71) Applicant: Mesoblast, Inc., New York, NY (US)

(72) Inventors: Silviu Itescu, Melbourne (AU); Ravi Krishnan, Royston Park (AU); Peter Ghosh, Fairlight (AU)

(73) Assignee: Mesoblast, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/036,402

(22) Filed: Jul. 16, 2018

(65) Prior Publication Data

US 2019/0046575 A1 Feb. 14, 2019

Related U.S. Application Data

(63) Continuation of application No. 14/650,171, filed as application No. PCT/AU2013/001454 on Dec. 12, 2013, now Pat. No. 10,028,979.

(60) Provisional application No. 61/736,352, filed on Dec. 12, 2012.

(51) Int. Cl.
*A61K 35/28* (2015.01)
*C12N 5/0775* (2010.01)

(52) U.S. Cl.
CPC ............ *A61K 35/28* (2013.01); *C12N 5/0663* (2013.01)

(58) Field of Classification Search
CPC .................................................. C12N 5/0663
See application file for complete search history.

(56) References Cited

U.S. PATENT DOCUMENTS

2009/0053182 A1 2/2009 Ichim et al.
2015/0306146 A1 10/2015 Itescu et al.

FOREIGN PATENT DOCUMENTS

WO WO 2004/084921 A1 10/2004
WO WO 2008/036374 A2 3/2008

OTHER PUBLICATIONS

Bonfield, T.L. et al. (2010), "Human mesenchymal stem cells suppress chronic airway inflammation in the murine ovalbumin asthma model", American Journal of Physiology Lung Cellular and Molecular Physiology, 299, L760-L770.
Notification of Transmittal of the International Search Report and the Written Opinion of the International Searching Authority, or the Declaration, including an International Search Report and Written Opinion of the International Searching Authority, dated Jan. 29, 2014 in connection with PCT International Application No. PCT/AU2013/001454.
Office Action dated Mar. 31, 2016 by the Singaporean Patent Office in connection with Singaporean Application No. 11201504352T.
Extended European Search Report dated Apr. 6, 2016 by the European Patent Office in connection with European Application No. 13862590.0.
Boxall and Jones (2012), "Markers for characterization of bone marrow and multipotential stromal cells", Stem Cells Int. vol. 2012, 12 pages.
Goodwin et al. (2011), "Bone Marrow-Derived Mesenchymal Stromal Cells Inhibit Th2-Mediated Allergic Airways Inflammation in Mice" Stem Cells 29:1137-1148.
Gronthos et al. (2007), "A Novel Monoclonal Antibody (STRO-3) Identifies an Isoform of Tissue Nonspecific Alkaline Phosphatase Expressed by Multipotent Bone Marrow Stromal Stem Cells" Stem Cells Dev. 16(6):953-963.
Kapoor et al. (2012), "Tolerance-like mediated suppression by mesenchymal stem cells in patients with dust mite allergy-induced asthma" J. Allergy Clin. Immunol. 129(4):1094-1101.
Karoubi et al. (2009), "Identification of mesenchymal stromal cells in human lung parenchyma capable of differentiating into aquaporin 5-expressing cells" Lab. Invest. 89(10):1190-1114.
Nemeth et al. (2010), "Bone marrow stromal cells use TGF-β to suppress allergic responses in a mouse model of ragweed-induced asthma" Proc. Nat'l Acad. Sci. U.S.A. 107(12); 5652-5657.

*Primary Examiner* — Bin Shen
(74) *Attorney, Agent, or Firm* — John P. White; Gary J. Gershik; Cooper & Dunham LLC

(57) ABSTRACT

The present disclosure provides methods of treating or preventing respiratory condition and/or for treating an IgE-mediated allergy and/or for reducing an allergic response to an allergen and/or for inducing anergy to an allergen in a subject and/or improving lung function in a subject suffering from an allergy comprising administering to a subject a population of cells enriched for STRO-1+ cells and/or progeny thereof and/or soluble factors derived therefrom.

19 Claims, 17 Drawing Sheets

METHODS OF TREATING OR PREVENTING RESPIRATORY CONDITIONS

RELATED APPLICATION DATA

This application is a continuation of U.S. application Ser. No. 14/650,171, filed Jun. 5, 2015, now U.S. Pat. No. 10,028,979, issued Jul. 24, 2018, which is a § 371 national stage of PCT International Application No. PCT/AU2013/001453, filed Dec. 12, 2013, and claims the benefit of U.S. Provisional Application No. 61/736,325, filed Dec. 12, 2012, the entire contents of each of which are hereby incorporated by reference.

FIELD

The present disclosure relates to methods for treating or preventing respiratory conditions, e.g., IgE-mediated allergic respiratory conditions.

INTRODUCTION

Respiratory conditions are recognized as encompassing pathological conditions affecting the organs and tissues involved in gas exchange, and includes conditions of the upper respiratory tract, trachea, bronchi, bronchioles, alveoli, pleura and pleural cavity, and the nerves and muscles of breathing. Chronic respiratory conditions cause approximately 7% of all deaths worldwide and represent about 4% of the global burden of disease. In the US alone, the cost of chronic respiratory conditions is estimated to be about US$154 billion annually, including direct and indirect costs. Respiratory conditions can be divided into several classes, including:

Inflammatory lung conditions, such as, asthma, cystic fibrosis, emphysema, chronic obstructive pulmonary disorder or acute respiratory distress syndrome, which are characterized by increased levels of neutrophils and/or inflammatory cytokines in the lungs of a subject;

obstructive lung conditions, such as chronic obstructive lung disease and asthma, which are characterized by a reduction in airway volume or impediment of free gas flow; and restrictive lung conditions (also known as interstitial lung diseases), such as infant respiratory distress syndrome, which as characterized by loss of lung compliance causing incomplete lung expansion and/or increased lung stiffness.

Asthma is a common chronic respiratory condition characterized by variable and recurring symptoms, reversible airway obstruction, airway (e.g., bronchial) hyperresponsiveness, and an underlying inflammation. Acute symptoms of asthma include cough, wheezing, shortness of breath and nocturnal awakening. These symptoms usually arise from bronchospasm and require and respond to bronchodilator therapy. Central to the pathophysiology of asthma is the presence of underlying airway inflammation mediated by the recruitment and activation of multiple cell types including mast cells, eosinophils, T lymphocytes, macrophages, dendritic cells and neutrophils. The mechanisms influencing airway hyperresponsiveness are multiple and include inflammation, dysfunctional neuroregulation, and airway remodeling. Airway remodeling involves structural changes including thickening of the sub-basement membrane, sub-epithelial fibrosis, airway smooth muscle hypertrophy and hyperplasia, blood vessel proliferation and dilation with consequent permanent changes in the airway that increase airflow obstruction and that is not prevented by or fully reversible by current therapies.

Current standard therapies for asthma are a combination of corticosteroids and β2-agonists (anti-inflammatory and bronchodilator drugs). These drugs provide acceptable control of the condition for many asthmatics. However, it is estimated that 5 to 10% of the asthma patients have symptomatic condition despite treatment with this combination of corticosteroids and β2-agonists (Chanez et al, J Allergy Clin Immunol 119:1337-1348 (2007)).

Chronic obstructive pulmonary disease (COPD) is the most common chronic lung condition associated with significant morbidity and mortality. In the United States, COPD is the fourth leading cause of death and accounts for more than $30 billion in annual health care costs. An estimated 16 million adults are affected by COPD, and each year about 120,000 Americans die of the condition. COPD is defined as a chronic disease characterized by airway/alveolar/systemic inflammation, with measured airflow obstruction (FEV1/FVC<70% and FEVi<80% predicted) that is partially improved with bronchodilator therapy. The local and systemic release of inflammatory mediators by the lung cells leads to airway disease (chronic obstructive bronchitis) and, in a minority of patients, to destruction of parenchymal tissue (emphysema), both of which can result in the airflow limitation that characterizes COPD. The release of these inflammatory mediators by the lung cells may also exacerbate inflammation in other organ systems, such as that observed in coronary, cerebrovascular, and peripheral vascular conditions.

Current therapies to treat COPD include bronchodilators, especially anticholinergic agents, that help to some degree decrease hyperinflation, therefore increasing inspiratory capacity and relieving dyspnea. Although corticosteroids are an effective treatment for most cases of asthma, the inflammatory cells and mediators in COPD are not sensitive to treatment with systemic or inhaled corticosteroids making treatment with these agents of limited usefulness in COPD.

Idiopathic pulmonary fibrosis (IPF) is a chronic, progressives fibrotic disorder of the lower respiratory tract that typically affects adults beyond the age of 40. IPF is thought to occur as a result of initial injury to the lung by environmental factors such as cigarette smoke leading to recruitment of neutrophils, lymphocytes and macrophages to the lung alveoli. Release of fibrogenic cytokines, such as TGF-β by alveolar epithelial cells results in fibroblast proliferation, migration, and fibrosis. These fibroblasts not only fill the respiratory space but also secrete collagen and matrix proteins in response to many cytokines leading to parenchymal remodeling (Shimizu et al., Am J Respir Crit Care Med 163:210-217 (2001)). This differentiation of fibroblasts is likely key to the chronic nature of IPF. These events lead to cough and progressive shortness of breath. IPF patients have compromised lung function and have shown restrictive lung volumes and capacities. Although corticosteroids, immunosupressive agents, neutrophil elastase inhibitor, hepatocyte growth factor, and interferon gamma-Ib have been proposed as treatment agents for IPF, no treatment other than lung transplantation is known to prolong survival and IPF remains a fatal disorder with a 3 to 6 yr median range of survival. Thus, the first line of treatment of IPF has not yet been established.

Other respiratory conditions include, but are not limited to, pulmonary arterial hypertension (PAH), pulmonary vasoconstriction, lymphangioleiomyomatosis (LAM), tuberous sclerosis complex (TSC), Acute Respiratory Distress Syndrome (ARDS) and Ventilator Induced Lung Injury (VILI).

It will be apparent to the skilled artisan from the foregoing disclosure that respiratory conditions are a prevalent and debilitating class of conditions for which there are limited options for treatment. Thus, new therapies for these conditions are desirable.

SUMMARY

The present inventors have now shown that using STRO-1$^+$ cell preparations they are able to reduce $T_H2$ mediated allergic responses (e.g., reduce eosinophils and/or IL-4 levels and/or IgE levels), e.g., an IgE-mediated allergic response as well as bronchial hyperresponsiveness in a dose dependent manner in an accepted animal model of a human respiratory condition, such as, asthma, e.g., allergic asthma. The inventors found that they could suppress either (or both) an early allergic reponse and/or a late allergic response. This dose responsiveness demonstrates that it is the STRO-1$^+$ cell preparations that is providing a therapeutic benefit.

The STRO-1$^+$ cell preparations additionally reduced eosinophil cell infiltration in the airway lumen and bronchoalveolar lavage fluid and neutrophil numbers in bronchoalveolar lavage fluid, demonstrating the ability of these preparations to suppress inflammation in the lung of a subject, e.g., subjects suffering from an inflammatory respiratory condition, such as, asthma.

The STRO-1$^+$ cell preparations additionally reduced allergen specific IgE levels in treated animals.

The inventors also observed that late phase asthmatic response, e.g., caused by migration of neutrophils and basophils to the respiratory system was improved in subjects receiving STRO-1$^+$ cell preparations. These observations indicate that STRO-1$^+$ cell preparations are useful for reducing or preventing damage to the respiratory system, e.g., inflammation and/or remodeling caused by neutrophils and basophils.

The findings by the inventors provide the basis for a method of treating or preventing a respiratory condition in a subject, the method comprising administering to the subject a population of cells enriched for STRO-1$^+$ cells and/or progeny thereof and/or soluble factors derived therefrom.

The present disclosure additionally provides a method of treating or preventing a IgE-mediated allergy (or a $T_H2$-mediated allergy) in a subject, the method comprising administering to the subject a population of cells enriched for STRO-1$^+$ cells and/or progeny thereof and/or soluble factors derived therefrom.

The present disclosure additionally provides a method for reducing an allergic response to an allergen and/or for inducing anergy to an allergen, the method comprising administering to the subject a population of cells enriched for STRO-1$^+$ cells and/or progeny thereof and/or soluble factors derived therefrom.

The present disclosure additionally provides a method for treating or preventing an allergic response to house dust mite allergen (HDM) or reducing an allergic response to HDM and/or for inducing anergy to HDM, the method comprising administering to the subject a population of cells enriched for STRO-1$^+$ cells and/or progeny thereof and/or soluble factors derived therefrom.

The present disclosure additionally provides a method for improving lung function in a subject, the method comprising administering to the subject a population of cells enriched for STRO-1$^+$ cells and/or progeny thereof and/or soluble factors derived therefrom, wherein the subject suffers from an allergy, an IgE-mediated allergy or an allergic response to HDM.

In one example, the respiratory condition is associated with excessive cell proliferation, remodeling, inflammation, vasoconstriction, bronchoconstriction, airway hyperreactivity and/or edema. For example, the disclosure provides methods for treating or preventing conditions such as asthma, chronic obstructive pulmonary disease, pulmonary arterial hypertension; acute respiratory distress syndrome, ventilator induced lung injury, cystic fibrosis, bronchiectasis, alpha-1-antitrypsin deficiency, rhinitis, rhino sinusitis, primary ciliary dyskinesia, pneumonia, bronchiolitis, interstitial lung disease including lymphangioleiomyomatosis, idiopathic pulmonary fibrosis, obliterative bronchiolitis or bronchiolitis obliterans, nonspecific interstitial pneumonia, cryptogenic organizing pneumonia, acute interstitial pneumonia, respiratory bronchiolitis-associated interstitial lung disease, or pulmonary sarcoidosis.

In one example, a lung or condition is an acute lung injury. For example, the acute lung injury is one or more of physical trauma, a chemical injury, e.g., a chemical burn, smoke inhalation, or exposure to a toxic substance. In another specific embodiment, said lung disease, disorder, or condition is an injury caused by a neoplastic or paraneoplastic disease.

In one example, the respiratory condition is chronic. In this regard, a method of the disclosure can be used to treat an early stage or late stage or both stages of a chronic respiratory condition.

In one example, the respiratory condition is an inflammatory respiratory condition, an obstructive respiratory condition or a restrictive respiratory condition.

In one example, the respiratory condition or allergy is a reversible airway obstruction.

In one example, the respiratory condition or allergy is an obstructive respiratory condition, such as, COPD, asthma, obliterative broncholitis or cystic fibrosis. In one example, the respiratory condition is asthma.

In one example, the respiratory condition is a restrictive respiratory condition, such as, a restrictive lung condition (e.g., extrinsic allergic alveolitis, fibrosing alveolitis, asbestosis or eosinophilic pneumonia) or a restrictive pleural condition (e.g., pleural effusion, pneumothorax or bronchiectasis).

In one example, the respiratory condition is not due to an infection or cancer.

In one example, the respiratory condition is an inflammatory condition. For example, the condition is associated with airway hyperreactivity and/or bronchial hyperreactivity and/or eosinophil cell infiltration in the airway lumen and bronchoalveolar lavage fluid. In this regard, in one example a method of the disclosure comprises administering a population of cells enriched for STRO-11 cells and/or progeny thereof and/or soluble factors derived therefrom such that airway hyperreactivity and/or bronchial hyperreactivity and/or eosinophil cell infiltration and/or neutrophil infiltration in the airway lumen and/or bronchoalveolar lavage fluid is reduced.

In one example, the condition is asthma, such as chronic asthma or acute asthma or allergic asthma. For example, the condition is chronic asthma or allergic asthma.

In one example, the condition is associated with remodeling of the lung, e.g., asthma or pulmonary fibrosis, such as, idiopathic pulmonary fibrosis.

In one example, the asthma is severe asthma and/or refractory asthma.

In one example, the condition is steroid refractory asthma. For example, a subject suffering from asthma is refractory to treatment with a steroid, e.g., a corticosteroid, such as flunisolide, mometasone furoate, triamcinolone, fluticasone, budesonide, beclomethasone dipropionate or a combination of any two or more of the foregoing.

In another example, the condition is long acting beta agonist (LABA) refractory asthma. For example, a subject suffering from asthma is refractory to treatment with a long acting beta agonist such as, for example, salmeterol, formoterol, bumbeterol or clenbuterol.

In another example, the condition is LABA and steroid refractory asthma.

In one example, the method reduces or prevents an early phase allergic or asthmatic response.

In another example, the method reduces or prevents a late phase allergic or asthmatic response.

In one example, the condition is a fibrotic condition. The fibrotic disease of the lung may be interstitial lung disease (diffuse parenchymal lung disease). In another example, the interstitial lung disease is silicosis, asbestosis, berylliosis, systemic sclerosis, polymyositis, or dermatomyositis. In other examples, the interstitial lung disease is caused by an antibiotic, a chemotherapeutic drug, an antiarrhythmic drug, or an infection.

In a further example, the condition is idiopathic pulmonary fibrosis.

In one example, a method as described herein in any example comprises administering a population of cells enriched for STRO-1$^{bright}$ cells and/or progeny thereof and/or soluble factors derived therefrom.

In one example, a method as described herein in any example comprises administering a population of cells enriched for STRO-1$^+$ and tissue non-specific alkaline phosphate$^+$ (TNAP)$^+$ cells and/or progeny thereof and/or soluble factors derived therefrom.

In one example, a method as described herein in any example comprises administering a population of cells enriched for tissue non-specific alkaline phosphate$^+$ (TNAP)$^+$ cells and/or progeny thereof and/or soluble factors derived therefrom. As shown herein, such cells are STRO-1$^+$, e.g., STRO-1$^{bright}$. In one example, the cells are enriched for STRO-3$^+$ cells.

In one example, the population enriched for STRO-1$^+$ cells and/or progeny thereof and/or soluble factors derived therefrom are administered systemically.

For example, the population and/or progeny and/or soluble factors are administered intravenously.

In another example, the population and/or progeny and/or soluble factors are administered intranasally or by inhalation.

In one example, the population and/or the progeny and/or the soluble factors are administered a plurality of times. In this regard, the present inventors have shown that a population of cells as described herein can provide a therapeutic benefit for up to four weeks or for at least four weeks. Accordingly, in one example, the population and/or the progeny and/or the soluble factors are administered once every three or more weeks. For example, the population and/or the progeny and/or the soluble factors are administered once every four or more weeks. For example, the population and/or the progeny and/or the soluble factors are administered once every five or more weeks. For example, the population and/or the progeny and/or the soluble factors are administered once every ten or more weeks. For example, the population and/or the progeny and/or the soluble factors are administered once every twelve or more weeks.

In one example, the method comprises monitoring the subject and administering a further dose of the population and/or the progeny and/or the soluble factors when one or more of the following occurs:

(i) a subject begins to persistently wheeze and/or cough and/or have chest tightness and/or have difficulty breathing;
(ii) a subject shows one or more of the following when assessed by spirometer:
   a) 20% difference on at least three days in a week for at least two weeks;
   b) ≥20% improvement of peak flow following treatment, for example:
      10 minutes of inhaled 3-agonist (e.g., salbutamol);
      six weeks of inhaled corticosteroid (e.g., beclometasone);
      14 days of 30 mg prednisolone.
   c) ≥20% decrease in peak flow following exposure to a trigger (e.g., exercise);
(iii) bronchoscopy showing abnormal cells and/or foreign substances and/or blockages in the respiratory tract of a subject; or
(iv) chest CT scan showing abnormalities of the blood vessels in the lungs, accumulation of blood or fluid in the lungs, bronchiectasis, pleural effusion or pneumonia.

In one example, a method described herein according to any example comprises administering a dose of the population and/or the progeny and/or the soluble factors sufficient to achieve one or more of the following:

(i) improved bronchial hyperresponsiveness, e.g., as assessed using a bronchial challenge test;
(ii) improved airway hyperresponsiveness;
(iii) reduced eosinophil infiltration of the lung or bronchoalveolar lavage fluid;
(iv) reduced neutrophil infiltration of the lung or bronchoalveolar lavage fluid;
(v) reduced late asthmatic response, e.g., as assessed by spirometer;
(vi) reduced early asthmatic response, e.g., as assessed by spirometer; and/or
(vii) reduced lung remodeling/fibrosis, e.g., as assessed by chest CT scan.

In one example, the dose is sufficient to achieve at least two or three or four of five or all of the foregoing.

In one example, a method described herein according to any example comprises administering between $1 \times 10^6$ to $150 \times 10^6$ STRO-1$^+$ cells and/or progeny thereof.

In one example, a method described herein according to any example comprises administering between $25 \times 10^6$ to $150 \times 10^6$ STRO-1$^+$ cells and/or progeny thereof. For example, the method comprises administering about $25 \times 10^6$ or $75 \times 10^6$ or $150 \times 10^6$ STRO-1$^+$ cells and/or progeny thereof.

In one example, a method described herein according to any example comprises administering between about $2.5 \times 10^4$ cells to $4.5 \times 10^6$ STRO-1$^+$ cells and/or progeny thereof per kg.

In one example, a method described herein according to any example comprises administering between about $4.5 \times 10^5$ to $4.5 \times 10^6$ STRO-1$^+$ cells and/or progeny thereof per kg. For example, the method comprises administering about $4.5 \times 10^5$ or about $5.5 \times 10^6$ or about $1.7 \times 10^6$ or about $1.9 \times 10^6$ or about $3.5 \times 10^6$ or about $4.5 \times 10^6$ STRO-1$^+$ cells and/or progeny thereof per kg.

In one example, a method described herein according to any example comprises administering a whole body dose of STRO-1$^+$ cells and/or progeny thereof and/or soluble factors derived therefrom. For example, when the cells or soluble factors are administered a plurality of times, the whole body dose remains constant.

For example, the method comprises administering 150×10$^6$ STRO-1$^+$ cells and/or progeny thereof in 10 mL to a subject, i.e., 1.5×10$^6$ STRO-1$^+$ cells and/or progeny thereof per mL.

In one example, a method described herein according to any example comprises administering to a subject suffering from steroid refractory asthma or LABA refractory asthma or steroid and LABA refractory asthma 150×10$^6$ STRO-1$^+$ cells and/or progeny thereof, e.g., in 10 mL to a subject, i.e., 1.5×10$^6$ STRO-1$^+$ cells and/or progeny thereof per mL.

In one example, a method described herein according to any example comprises administering to a subject suffering from idiopathic pulmonary fibrosis 150×10$^6$ STRO-1$^+$ cells and/or progeny thereof, e.g., in 10 mL to a subject, i.e., 1.5×10$^6$ STRO-1$^+$ cells and/or progeny thereof per mL.

In one example, the population and/or the progeny cells are autogeneic or allogeneic and/or the soluble factors can be derived from autogeneic or allogeneic cells. In one example, the population and/or the progeny are allogeneic and/or the soluble factors are from allogeneic cells.

In accordance with the above example, the method can additionally comprise obtaining the population and/or progeny cells and/or soluble factors or can additionally comprise isolating the population and/or progeny cells and/or soluble factors. In one example, the population and/or progeny cells are based on expression of STRO-1 and/or TNAP.

In one example, the population and/or progeny cells and/or soluble factors are obtained from the subject being treated. In another example, the population and/or progeny cells and/or soluble factors are obtained from a different subject of the same species.

In one example, the population enriched for STRO-1$^+$ cells and/or progeny cells have been culture expanded prior to administration and/or prior to obtaining the soluble factors.

In accordance with the above example, a method as described herein according to any example can additionally comprise culturing the population and/or progeny cells.

In one example, the STRO-1$^+$ cells and/or progeny cells thereof and/or soluble factors derived therefrom are administered in the form of a composition comprising said STRO-1$^+$ cells and/or progeny cells thereof and/or soluble factors derived therefrom and a carrier and/or excipient.

In accordance with the above example, a method as described herein according to any example can additionally comprise formulating the population and/or progeny and/or soluble factors into a composition.

In one example, the subject is suffering from a respiratory condition or an exacerbation thereof (e.g., an asthma attack) at the time of treatment. For example, the subject is in need of treatment.

In one example, the subject has a respiratory condition, however is not actively suffering from the respiratory condition or an exacerbation thereof (e.g., an asthma attack) at the time of treatment, i.e., the method is a method of preventing the condition or an exacerbation thereof.

The present disclosure also provides a population of cells enriched for STRO-1$^+$ cells and/or progeny thereof and/or soluble factors derived therefrom for use in the treatment or prevention of a respiratory condition.

The present disclosure also provides for use of a population of cells enriched for STRO-1$^+$ cells and/or progeny thereof and/or soluble factors derived therefrom in the manufacture of a medicament for treating or preventing a respiratory condition in a subject.

The present disclosure also provides a kit comprising a population of cells enriched for STRO-1$^+$ cells and/or progeny thereof and/or soluble factors derived therefrom packaged with instructions for use in a method described herein according to any example.

For example, the present disclosure provides a kit comprising a composition comprising the population and/or the progeny and/or the soluble factors packaged with product information indicating use of the composition in a method described herein according to any example.

DETAILED DESCRIPTION

General Techniques and Selected Definitions

Figure 1:
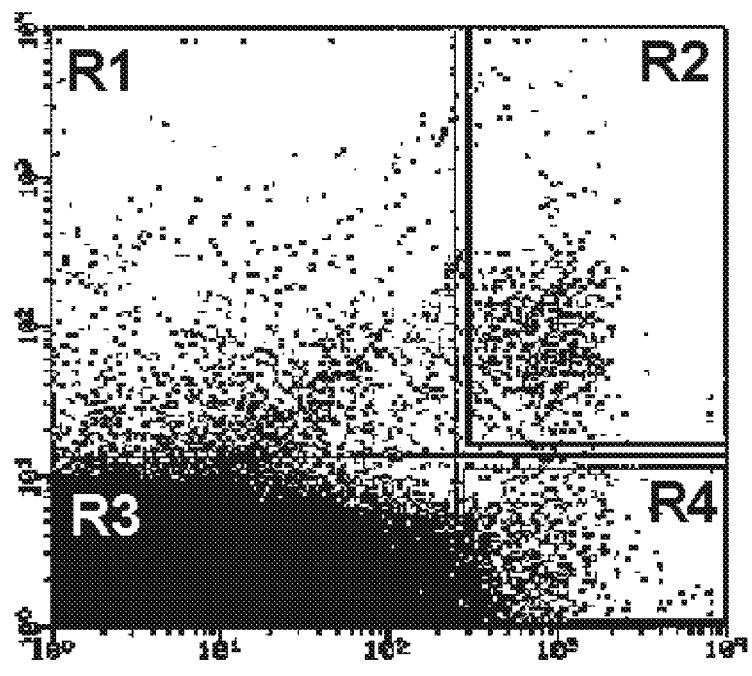
FIG. 1. Co-expression of TNAP (STRO-3) and the Mesenchymal Precursor Cell Marker, STRO-1$^{bright}$ by Adult Human bone marrow morphonuclear cells (BMMNC). Dual-color immunofluorescence and flow cytometry was performed by incubation of STRO-1 MACS-selected BMMNC and indirectly labeled with a goat anti-murine IgM antibody coupled to FITC (x axis), and STRO-3 mAb (murine IgG1) indirectly labeled with a goat anti-murine IgG coupled to PE (y axis). The dot plot histogram represents 5×10$^4$ events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1$^+$ cells failed to react with the STRO-3 mAb.
Figure 2:
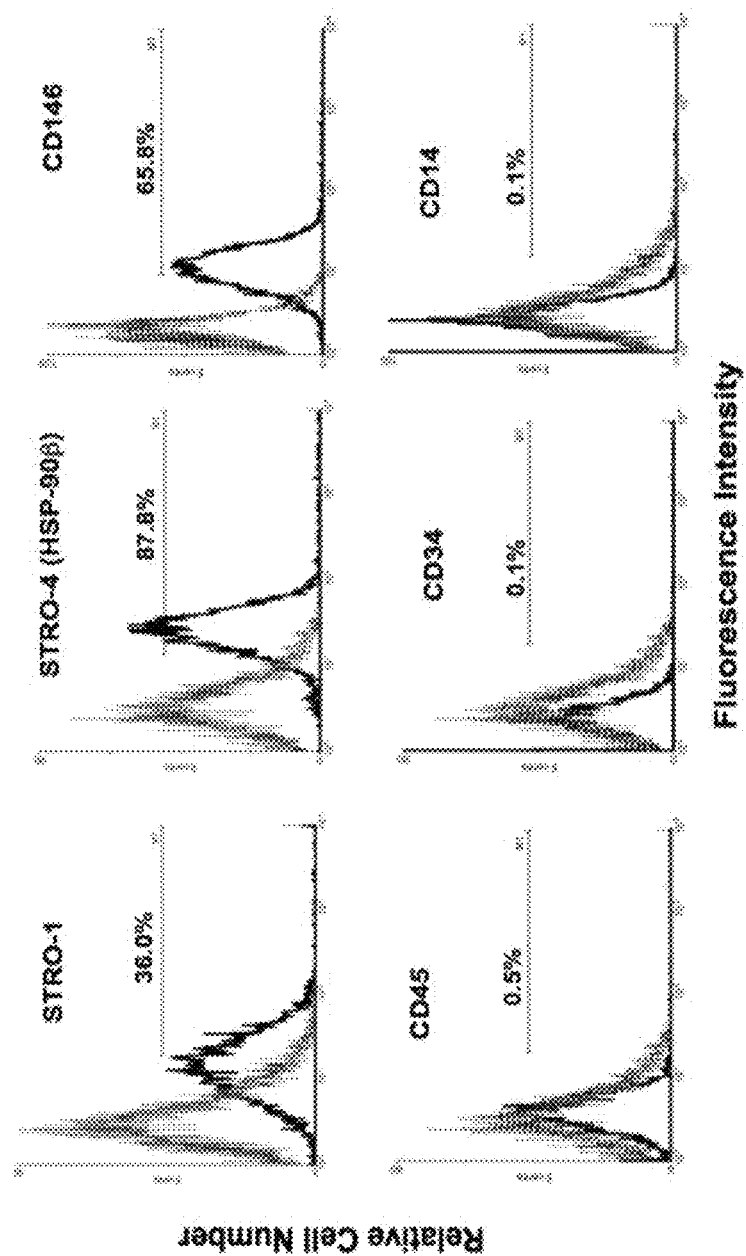
FIG. 2. Graphical representations showing representative flow cytometric histograms produced using single cell suspensions of culture expanded bone marrow derived cynomolgus MPCs with positive cell surface expression of the mesenchymal stem cell markers, STRO-1, STRO-4 and CD146 (solid) relative to the isotype (IgM, IgG2a and IgG1) negative controls (hashed) detected using goat anti-murine IgM or IgG conjugated-FITC secondary antibodies. Representative histograms also show that cynomolgus MPCs lack cell surface expression for markers of monocyte/macrophage (CD14), haematopietic stem/progenitor cells (CD34) and mature leukocyte (CD45). Levels of greater than 1% fluorescence compared to the isotype control signify positivity.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example of the disclosure unless specifically stated otherwise.

Those skilled in the art will appreciate that the present disclosure and individual examples thereof are susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples of the disclosure included herein, which are intended for the purpose of exemplification only. Functionally-equivalent products, compositions and methods are clearly within the scope of the disclosure and examples thereof, as described herein.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). *Biochem. Biophys. Res. Commun.* 73 336-342; Merrifield, R. B. (1963). J Am. Chem. Soc. 85, 2149-2154; Barany, G. and Merrifield, R. B. (1979) in The Peptides (Gross, E. and Meienhofer, J. eds.), vol. 2, pp. 1-284, Academic Press, New York. 12. Wtinsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) hIt. *J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified integer may be obtained from a particular source albeit not necessarily directly from that source. In the context of soluble factors derived from STRO-1$^+$ cells and/or progeny cells thereof, this term shall be taken to mean one or more factors, e.g., proteins, peptides, carbohydrates, etc, produced during in vitro culturing of STRO-1$^+$ cells and/or progeny cells thereof.

The term "respiratory condition" shall be taken to include any disease or condition that reduces lung function in a subject and includes, for example, asthma, chronic bronchitis, emphysema, cystic fibrosis, respiratory failure, pulmonary oedema, pulmonary embolism, pulmonary hypertension (high blood pressure), pneumonia and tuberculosis (TB), lung cancer, stiffening and scarring of lungs (e.g., caused by caused by drugs, poisons, infections, or radiation), lung disorders from unusual atmospheric pressure (e.g., caused by a mechanical ventilator). In one example, the respiratory condition is a chronic lung condition and/or a lung condition associated with inflammation in the lung, e.g., the lung condition is asthma COPD or cystic fibrosis or pulmonary fibrosis or bronchiolitis or alveolitis or vasculitis or sarcoidosis. In another example, the condition is associated with remodeling or fibrosis of a subject's lungs, e.g., the condition is pulmonary fibrosis (e.g., idiopathic pulmonary fibrosis) or asthma.

As used herein the term "asthma" will be understood to mean a disease characterized by paroxysmal or persistent symptoms of dyspnea, chest tightness, wheezing, sputum production and cough, associated with variable airflow limitation and airway hyperresponsiveness to endogenous or exogenous stimuli (Canadian Asthma Consensus Guidelines) and/or a condition characterized by airway hyperresponsiveness that leads to recurrent episodes of wheezing, breathlessness, chest tightness, and coughing, particularly at night or in the early morning along with variable airflow obstruction which is often reversible either spontaneously or with treatment (The Global Initiative for Asthma).

As used herein, the term "severe asthma" will be understood to mean well controlled asthma symptoms on high to very high doses of inhaled corticosteroids, with or without the use of oral corticosteroids; and "very severe asthma" will be understood to mean well or not well controlled asthma symptoms despite very high dose of inhaled and ingested corticosteroids and with or without requiring additional therapies. For these definitions, the daily high and very high doses of inhaled corticosteroid (approximate equivalent doses) are defined as follows: High dose is beclomethasone diproprionate, 1000 to 2000 μg; fluticasone, 500 to 1000 μg; and budesonide, 800 to 1600 μg and very high dose is fluticasone, 1000 to 2000 μg and budesonide, 1600-3200 μg.

As used herein, the term "refractory asthma" includes patients with "fatal" or "near fatal" asthma as well as the asthma subgroups previously described as "severe asthma" and "steroid-dependent and/or resistant asthma," "difficult to control asthma," "poorly controlled asthma," "brittle asthma," or "irreversible asthma." Refractory asthma can be defined as per the American Thoracic Society guidelines when one or both major criteria and two minor criteria, described as follows, are fulfilled. The major criteria are: In order to achieve control to a level of mild-moderate persistent asthma: (1) Treatment with continuous or near continuous (?50% of year) oral corticosteroids 2) Requirement for treatment with high-dose inhaled corticosteroids. The minor criteria are: (1) Requirement for daily treatment with a controller medication in addition to inhaled corticosteroids e.g., LABA, theophylline or leukotriene antagonist (2) Asthma symptoms requiring short-acting β-agonist use on a daily or near daily basis (3) Persistent airway obstruction ($FEV_1$<80% predicted; diurnal peak expiratory flow (PEF) variability >20%) (4) One or more urgent care visits for asthma per year (5) Three or more oral steroid "bursts" per year (6) Prompt deterioration with <25% reduction in oral or inhaled corticosteroid dose (7) Near fatal asthma event in the past. For the purposes of definition of refractory asthma, the drug (μg/d) and the dose (puffs/d) are as follows: (a) Beclomethasone dipropionate >1,260>40 puffs (42 μg/inhalation)>20 puffs (84 μg/inhalation); (b) Budesonide >1,200>6 puffs; (c) Flunisolide >2,000>8 puffs; (d) Fluticasone propionate >880>8 puffs (110 μg), >4 puffs (220 μg); (e) Triamcinolone acetonide >2,000>20 puffs.

As used herein, the term "acute asthma" or "allergic asthma" refers to asthma triggered by allergens (e.g., dust mite feces or pollen) activating mast cells located beneath the mucosa of the lower airways of respiratory tract. Activation of mast cells triggers release of granules that stimulate the nasal epithelium to produce mucus and subsequent contraction of smooth muscle within the airway. This contraction of smooth muscle constricts the airway, causing the characteristic asthmatic wheezing.

"Chronic asthma" is not caused by allergens, but rather a result of the inflammation obtained from acute asthma. The overall effects of acute asthma causes chronic inflammation, which causes the mucosal epithelium to become hypersensitive to environmental responses. So simple environmental agents, such as smoke, can stimulate the hypersensitive epithelium to produce large amounts of mucous and constrict.

As used herein, the term "idiopathic pulmonary fibrosis" shall be understood to mean a chronic, progressive form of lung disease of unknown origin characterized by fibrosis of the supporting framework (interstitium) of the lungs. Common symptoms are progressive dyspnea (difficulty breathing), but also include dry cough, clubbing (a disfigurement of the fingers), and rales (a crackling sound in the lungs during inhalation, heard with a stethoscope). The 2002 ATS/ERS Multidisciplinary Consensus Statement on the Idiopathic Interstitial Pneumonias proposed the following criteria for establishing the diagnosis of IPF without a lung biopsy:

Major criteria (all 4 required):
Exclusion of other known causes of interstitial lung disease (drugs, exposures, connective tissue diseases);
Abnormal pulmonary function tests with evidence of restriction (reduced vital capacity) and impaired gas exchange (pO2, p(A-a)O2, DLCO);
Bibasilar reticular abnormalities with minimal ground glass on high-resolution CT scans; and
Transbronchial lung biopsy or bronchoalveolar lavage (BAL) showing no features to support an alternative diagnosis.

Minor criteria (3 of 4 required):
Age ≥50;
Insidious onset of otherwise unexplained exertional dyspnea;
Duration of illness ≥3 months; and
Bibasilar inspiratory crackles.

The term "exacerbation" shall be understood to mean an exaggeration of a respiratory symptoms of a respiratory condition, e.g., an asthma attack.

An "early phase allergic response" (or asthmatic response) typically occurs within 2 hours, or one hour or 30 minutes or 10 minutes or 1 minute following allergen exposure and is also commonly referred to as the immediate allergic reaction or as a Type I allergic reaction. The reaction is caused by the release of histamine and mast cell granule proteins by a process called degranulation, as well as the production of leukotrienes, prostaglandins and cytokines, by mast cells following the cross-linking of allergen specific IgE molecules bound to mast cell FcεRI receptors. These mediators affect nerve cells causing itching, smooth muscle cells causing contraction (leading to the airway narrowing seen in allergic asthma), goblet cells causing mucus production, and endothelial cells causing vasodilatation and edema.

A "late phase allergic response" (or asthmatic response) generally develops about 6-12 hours or 8-12 hours after allergen exposure and is mediated by, e.g., mast cells). The products of the early phase reaction include chemokines and molecules that act on endothelial cells and cause them to express Intercellular adhesion molecule (such as vascular cell adhesion molecule and selectins), which together result in the recruitment and activation of leukocytes from the blood into the site of the allergic reaction. Typically, the infiltrating cells observed in allergic reactions contain a high proportion of lymphocytes, and especially, of eosinophils. The recruited eosinophils will degranulate releasing a number of cytotoxic molecules (including Major Basic Protein and eosinophil peroxidase) as well as produce a number of cytokines such as IL-5. The recruited T-cells are typically of the Th2 variety and the cytokines they produce lead to further recruitment of mast cells and eosinophils, and in plasma cell isotype switching to IgE which will bind to the mast cell FcεRI receptors and prime the individual for further allergic responses As used herein, the term "effective amount" shall be taken to mean a sufficient quantity of STRO-1$^+$ cells and/or progeny cells thereof and/or soluble factors derived therefrom to reduce one or more symptoms of a respiratory condition as described herein.

As used herein, the term "therapeutically effective amount" shall be taken to mean a sufficient quantity of STRO-1$^+$ cells and/or progeny cells thereof and/or soluble factors derived therefrom to treat a respiratory condition, i.e., such that the subject no longer satisfies the clinical criteria for a respiratory condition or an exacerbation thereof.

As used herein, the term "prophylactically effective amount" shall be taken to mean a sufficient quantity of STRO-1$^+$ cells and/or progeny cells thereof and/or soluble factors derived therefrom to prevent or inhibit or delay the onset of a respiratory condition or an exacerbation thereof or a relapse thereof.

As used herein, the term "whole body dose" will be understood to mean that subjects are administered a specified dose of cells and/or soluble factors irrespective of their body weight or body surface area.

As used herein, the term "treat" or "treatment" or "treating" shall be understood to mean administering a therapeutically effective amount of soluble factors and/or cells and reducing or inhibiting symptom(s) of a respiratory condition such that the subject is no longer clinically diagnosed with the condition or an exacerbation thereof.

As used herein, the term "prevent" or "preventing" or "prevention" shall be taken to mean administering a prophylactically effective amount of soluble factors and/or cells and stopping or hindering or delaying the development or progression of a respiratory condition or exacerbation thereof. Preventing a respiratory condition also encompasses administering a prophylactically effective amount of soluble factors and/or cells and preventing or reducing the frequency of exacerbations of the condition.

As used herein, the term "soluble factors" shall be taken to mean any molecule, e.g., protein, peptide, glycoprotein, glycopeptide, lipoprotein, lipopeptide, carbohydrate, etc. produced by STRO-1$^+$ cells and/or progeny thereof that are water soluble. Such soluble factors may be intracellular and/or secreted by a cell. Such soluble factors may be a complex mixture (e.g., supernatant) and/or a fraction thereof and/or may be a purified factor. In one example, soluble factors are or are contained within supernatant. Accordingly, any example herein directed to administration of one or more soluble factors shall be taken to apply mutatis mutandis to the administration of supernatant.

As used herein, the term "supernatant" refers to the non-cellular material produced following the in vitro culturing of STRO-1$^+$ cells and/or progeny thereof in a suitable medium, for example, liquid medium. Typically, the supernatant is produced by culturing the cells in the medium under suitable conditions and time, followed by removing the cellular material by a process such as centrifugation. The supernatant may or may not have been subjected to further purification steps before administration. In one example, the supernatant comprises less than $10^5$, more such as, less than $10^4$, for example, less than 103, e.g., no live cells.

As used herein, the term "normal or healthy individual" shall be taken to mean a subject that does not suffer from a respiratory condition as assessed by any method known in the art and/or described herein. In one example, a "normal or healthy individual" does not suffer from any of the symptoms of a respiratory condition.

Allergens

In one example, the present disclosure provides a method for reducing or preventing a response (e.g., an allergic response) to an allergen. As used herein the term "allergen" shall be taken to mean a substance that comprises one or more antigens that are capable of inducing specific IgE formation (i.e., an allergic response). Following production of IgE, the IgE is bound to a Fc receptor on the surface of a mast cell or a basophil. Following subsequent exposure to the allergen, at least two IgE antibodies binding to at least two epitopes in the allergen causes cross-linking of the Fab' regions of the IgE molecules resulting in mast cell or basophil release of a variety of vasoactive amine, such as, for example, histamine, thereby inducing allergic symptoms. The term allergen includes all types of allergen, for example a polypeptide allergen, a phospholipid allergen, a fatty acid or a carbohydrate. Examples of common allergens are set forth in Table 1.

TABLE 1

Common allergens isolated from organisms

| | Allergen source | | |
|---|---|---|---|
| | Systematic name | Former name(s) | MW |
| Asterales | *Ambrosia artemisiifolia* (short ragweed) | | |
| | Amb a 1 | antigen E | 38 |
| | Amb a 2 | antigen K | 38 |
| | Amb a 3 | Ra3 | 11 |
| | Amb a 5 | Ra5 | 5 |
| | Amb a 6 | Ra6 | 10 |
| | Amb a 7 | Ra7 | 12 |
| | Amb a ? | | 11 |
| | *Ambrosia trifida* (giant ragweed) | | |
| | Amb t 5 | Ra5G | 4.4 |
| | *Artemisia vulgaris* (mugwort) | | |
| | Art v 2 | | 35 |
| Poales | *Cynodon dactylon* (Bermuda grass) | | |
| | Cyn d 1 | | 32 |
| | *Dactylis glomerata* (orchard grass) | | |
| | Dac g 1 | AgDg1 | 32 |
| | Dac g 2 | | 11 |
| | Dac g 5 | | 31 |
| | *Lolium perenne* (rye grass) | | |
| | Lol p 1 | Group I | 27 |
| | Lol p 2 | Group II | 11 |
| | Lol p 3 | Group III | 11 |
| | Lol p 5 | | 31 |
| | Lol p 9 | Lol p Ib | 31/35 |
| | *Phleum pratense* (timothy grass) | | |
| | Phl p 1 | | 27 |
| | Phl p 5 | Ag25 | 32 |
| | *Poa pratensis* (Kentucky blue grass) | | |
| | *Poa* p 1 | Group I | 33 |
| | *Poa* p 5 | | 31 |
| | *Poa* p 9 | | 32/34 |
| | *Sorghum halepense* (Johnson grass) | | |
| | Sor h 1 | | |
| Fagales | *Alnus glutinosa* (alder) | | |
| | Aln g 1 | | 17 |
| | *Betula verrucosa* (birch) | | |
| | Bet v 1 | | 17 |
| | Bet v 2 | profilin | 15 |
| | *Carpinus betulus* (hornbeam) | | |
| | Car b 1 | | 17 |
| | *Corylus avellana* (hazel) | | |
| | Cor a 1 | | 17 |
| | *Quercus alba* (white oak) | | |
| | Que a 1 | | 17 |

TABLE 1-continued

Common allergens isolated from organisms

| | Allergen source | | |
|---|---|---|---|
| | Systematic name | Former name(s) | MW |
| Pinales | *Cryptomeria japonica* (sugi) | | |
| | Cry j 1 | | 41-45 |
| | Cry j 2 | | |
| | *Juniper sabinoides* (mountain cedar) | | |
| | Jun s 1 | | 50 |
| | *Juniper virginiana* (eastern red cedar) | | |
| | Jun v 1 | | 45-50 |
| Oleales | *Olea europea* (olive) | | |
| | Ole e 1 | | 16 |
| | *Dermatophagoides pteronyssinus* (mite) | | |
| | Der p 1 | Antigen P1 | 25 |
| | Der p 2 | | 14 |
| | Der p 3 | trypsin | 28/30 |
| | Der p 4 | amylase | 60 |
| | Der p 5 | | 14 |
| | Der p 6 | chymotrypsin | 25 |
| | Der p 7 | | 22-28 |
| | *Dermatophagoides microceras* (mite) | | |
| | Der m 1 | | 25 |
| | *Dermatophagoides farinae* (mite) | | |
| | Der f 1 | | 25 |
| | Der f 2 | | 14 |
| | Der f 3 | | 30 |
| | *Lepidoglyphus destructor* (storage mite) | | |
| | Lep d ? | | 15 |
| | *Canis familiaris* (dog) | | |
| | Can f 1 | | 25 |
| | Can f 2 | | 27 |
| | *Felis domesticus* (cat saliva) | | |
| | Fel d 1 | cat-1 | 38 |
| | *Mus musculus* | | |
| | *Mus* m 1 | MUP | 19 |
| | *Rattus norvegius* | | |
| | Rat n 1 | | 17 |
| | *Aspergillus fumigatus* | | |
| | Asp f 1 | | 18 |
| | Asp f ? | | 90 |
| | Asp f ? | | 55 |
| | *Candida albicans* | | |
| | Cand a | | 40 |
| | *Alternaria alternata* | | |
| | Alt a 1 | | 28 |
| | *Trichophyton tonsurans* | | |
| | Tri t 1 | | 30 |
| | *Blattaria germanica* (cockroach) | | |
| | Bla g 2 | | 20 |

In one example, the allergen is from an animal, e.g., a mammal, e.g., a dog or a cat or a rat or a mouse.

In one example, the allergen is from a plant, e.g., plant pollen.

In one example, the allergen is from an insect, e.g., a mite.

In one example, the allergen is HDM.

STRO-1$^+$ Cells or Progeny Cells, and Supernatant or One or More Soluble Factors Derived Therefrom STRO-1$^+$ cells are cells found in bone marrow, blood, deciduous teeth (e.g., exfoliated deciduous teeth), dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum.

In one example, STRO-1$^+$ cells are capable of differentiating into one or more or two or more and/or three germ lines such as mesoderm and/or endoderm and/or ectoderm.

In one example, the STRO-1$^+$ cells are multipotential cells which are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. STRO-1$^+$ multipotential cells are thus non-hematopoietic progenitor cells which divide to yield daughter cells that are either stem cells or are precursor cells which in time will irreversibly differentiate to yield a phenotypic cell.

In one example, the STRO-1$^+$ cells are enriched from a sample obtained from a subject, e.g., a subject to be treated or a related subject or an unrelated subject (whether of the same species or different). The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1$^+$ cells comprises at least about 0.1% or 0.5% or 1% or 2% or 5% or 10% or 15% or 20% or 25% or 30% or 50% or 75% STRO-1$^+$ cells. In this regard, the term "population of cells enriched for STRO-1$^+$ cells" will be taken to provide explicit support for the term "population of cells comprising X % STRO1$^+$ cells", wherein X % is a percentage as recited herein.

The STRO-1$^+$ cells can, in some examples, form clonogenic colonies, e.g. CFU-F (fibroblasts) or a subset thereof (e.g., 50% or 60% or 70% or 70% or 90% or 95%) can have this activity.

In one example, the population of cells is enriched from a cell preparation comprising STRO-1$^+$ cells in a selectable form. In this regard, the term "selectable form" will be understood to mean that the cells express a marker (e.g., a cell surface marker) permitting selection of the STRO-1$^+$ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1$^+$ does not mean that the cells are selected by STRO-1 expression. In one example, the cells are selected based on at least STRO-3 expression, e.g., they are STRO-3$^+$ (TNAP$^+$).

Reference to selection of a cell or population thereof does not require selection from a specific tissue source. As described herein STRO-1$^+$ cells can be selected from or isolated from or enriched from a large variety of sources. That said, in some examples, these terms provide support for selection from any tissue comprising STRO-1$^+$ cells (e.g., MPCs) or vascularized tissue or tissue comprising pericytes (e.g., STRO-1$^+$ pericytes) or any one or more of the tissues recited herein.

In one example, the cells used in methods of the present disclosure express one or more markers individually or collectively selected from the group consisting of TNAP$^+$, VCAM-1$^+$, THY-1$^+$, STRO-2$^+$, STRO-4$^+$ (HSP-90β), CD45$^+$, CD146$^+$, 3G5$^+$ or any combination thereof.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

For example, the STRO-1$^+$ cells are STRO-1$^{bright}$ (syn. STRO-1$^{bright}$). In one example, the Stro-1$^{bright}$ cells are preferentially enriched relative to STRO-1$^{dim}$ or STRO-1$^{intermediate}$ cells.

In one example, the STRO-1$^{bright}$ cells are additionally one or more (or all) of TNAP$^+$, VCAM-1$^+$, THY-1$^+$, STRO-2$^+$, STRO-4$^+$ (HSP-90β) and/or CD146$^+$. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the mesenchymal precursor cells are perivascular mesenchymal precursor cells as defined in WO 2004/85630.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labeled or is undetectable above background levels, e.g., levels detected suing an isotype control antibody.

The term "bright", when used herein, refers to a marker on a cell surface that generates a relatively high signal when detectably labeled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labeled with a FITC-conjugated STRO-1 antibody as determined by fluorescence activated cell sorting (FACS) analysis, than non-bright cells (STRO-1$^{dull/dim}$). In one example, "bright" cells constitute at least about 0.1% of the most brightly labeled cells (e.g., bone marrow mononuclear cells) contained in the starting sample. In other examples, "bright" cells constitute at least about 0.1%, at least about 0.5%, at least about 1%, at least about 1.5%, or at least about 2%, of the most brightly labeled cells, e.g., bone marrow mononuclear cells contained in the starting sample. In one example, STRO-1$^{bright}$ cells have 2 log magnitude higher expression of STRO-1 surface expression relative to "background", namely cells that are STRO-1⁻. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in a preferred example, the STRO-1⁺ cells are capable of giving rise to clonogenic CFU-F.

In one example, a significant proportion of the STRO-1⁺ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another example, the STRO-1⁺ cells are not capable of giving rise, upon culturing, to hematopoietic cells.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used. In another useful example of the disclosure, cells of a non-human animal (or if the patient is not a human, from another species) are used.

The present disclosure also contemplates use of supernatant or soluble factors obtained or derived from STRO-1⁺ cells and/or progeny cells thereof (the latter also being referred to as expanded cells) which are produced from in vitro culture. Expanded cells of the disclosure may a have a wide variety of phenotypes depending on the culture conditions (including the number and/or type of stimulatory factors in the culture medium), the number of passages and the like. In certain examples, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an example, progeny cells useful for the methods of the disclosure are obtained by isolating TNAP⁺ STRO-1⁺ cells from bone marrow using magnetic beads labeled with the STRO-3 antibody, and then culture expanding the isolated cells (see Gronthos et al. *Blood* 85: 929-940, 1995 for an example of suitable culturing conditions).

In one example, such expanded cells (progeny) (for example, after at least 5 passages) can be TNAP⁻, CC9⁺, HLA class I⁺, HLA class II⁻, CD14⁻, CD19⁻, CD3⁻, CD11a⁻c⁻, CD31⁻, CD86⁻, CD34⁻ and/or CD80⁻. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9⁻). In one example, expanded cells still have the capacity to differentiate into different cell types.

In one example, an expended cell population used to obtain supernatant or soluble factors, or cells per se, comprises cells wherein at least 25%, e.g., at least 50%, of the cells are CC9⁺.

In another example, an expanded cell population used to obtain supernatant or soluble factors, or cells per se, comprises cells wherein at least 40%, e.g., at least 45%, of the cells are STRO-1⁺.

In a further example, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD10, CD13, SCF, PDGF-R, EGF-R, IGF1-R, NGF-R, FGF-R, Leptin-R (STRO-2=Leptin-R), RANKL, STRO-4 (HSP-903), STRO-1$^{bright}$ and CD146 or any combination of these markers.

In one example, the progeny cells are Multipotential Expanded STRO-1⁺ Multipotential cells Progeny (MEVI-MPs) as defined and/or described in WO 2006/032092. Methods for preparing enriched populations of STRO-1⁺ multipotential cells from which progeny may be derived are described in WO 01/04268 and WO 2004/085630. In an in vitro context STRO-1⁺ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MPCs from which progeny are derived may be directly harvested from a tissue source, or alternatively it may be a population that has already been expanded ex vivo.

For example, the progeny may be obtained from a harvested, unexpanded, population of substantially purified STRO-1⁺ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-4 (HSP-90β), STRO-1$^{bright}$, 3G5$^+$, VCAM-1, THY-1, CD146 and STRO-2.

MEMPS can be distinguished from freshly harvested STRO-1$^+$ multipotential cells in that they are positive for the marker STRO-1$^{bri}$ and negative for the marker Alkaline phosphatase (ALP). In contrast, freshly isolated STRO-1$^+$ multipotential cells are positive for both STRO-1$^{br}$ and ALP. In one example of the present disclosure, at least 15%, 20%, 30%, 40%, 50%, 60%, 70%, 80%, 90% or 95% of the administered cells have the phenotype STRO-1$^{bri}$, ALP$^-$. In a further example the MEMPS are positive for one or more of the markers Ki67, CD44 and/or CD49c/CD29, VLA-3, α3β1. In yet a further example the MEMPs do not exhibit TERT activity and/or are negative for the marker CD18.

The STRO-1$^+$ cell starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing methods described in the present disclosure, separation of cells carrying any given cell surface marker can be effected by a number of different methods, however, exemplary methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, for example monoclonal antibodies or based on monoclonal antibodies (e.g., proteins comprising antigen binding fragments thereof) because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. For example, the separation techniques maximize the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

In one example, the method for isolating STRO-1$^+$ cells comprises a first step being a solid phase sorting step utilizing for example magnetic activated cell sorting (MACS) recognizing high level expression of STRO-1. A second sorting step can then follow, should that be desired, to result in a higher level of precursor cell expression as described in patent specification WO 01/14268. This second sorting step might involve the use of two or more markers.

The method obtaining STRO-1$^+$ cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1$^+$ cell population has been obtained, it may be cultured or expanded by any suitable means to obtain MEMPs.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used to obtain the supernatant or soluble factors. In another useful example of the disclosure, cells of a non-human animal (or if the patient is not a human, from another species) are used to obtain supernatant or soluble factors.

Methods and uses of the present disclosure can be practiced using cells from any non-human animal species, including but not limited to non-human primate cells, ungulate, canine, feline, lagomorph, rodent, avian, and fish cells. Primate cells with which methods of the disclosure may be performed include but are not limited to cells of chimpanzees, baboons, cynomolgus monkeys, and any other New or Old World monkeys. Ungulate cells with which the disclosure may be performed include but are not limited to cells of bovines, porcines, ovines, caprines, equines, buffalo and bison.

Rodent cells with which the disclosure may be performed include but are not limited to mouse, rat, guinea pig, hamster and gerbil cells. Examples of lagomorph species with which the disclosure may be performed include domesticated rabbits, jack rabbits, hares, cottontails, snowshoe rabbits, and pikas. Chickens (*Gallus gallus*) are an example of an avian species with which methods of the disclosure may be performed.

In one example, the cells are human cells.

Cells useful for the methods of the disclosure may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present disclosure. In one example, the cells are maintained and stored by using cryo-preservation.

Genetically-Modified Cells

In one example, the STRO-1$^+$ cells and/or progeny cells thereof are genetically modified, e.g., to express and/or secrete a protein of interest. For example, the cells are engineered to express a protein useful in the treatment of a respiratory condition, such as, a protease, a DNAse or a surfactant protein, e.g., surfactant protein C.

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply mutatis mutandis to the present example of the disclosure.

In one example, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present disclosure, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the disclosure will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for methods of the present disclosure in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Life Technologies Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

Alternatively, an expression construct of the disclosure is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al., *J Virol.* 56:2731-2739 (1992); Johann et al, *J. Virol.* 65:1635-1640 (1992); Sommerfelt et al, *Virol.* 76:58-59 (1990); Wilson et al, *J. Virol.* 63:274-2318 (1989); Miller et al., *J. Virol.* 65:2220-2224 (1991); PCT/US94/05700; Miller and Rosman Bio-Techniques 7:980-990, 1989; Miller, A. D. *Human Gene Therapy* 7:5-14, 1990; Scarpa et al *Virology* 75:849-852, 1991; Burns et al. *Proc. Natl. Acad. Sci USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al. *Molec. Cell. Biol.* 5:3988-3996, 1988; Vincent et al. (1990) Vaccines 90 (Cold Spring Harbor Laboratory Press); Carter *Current Opinion in Biotechnology* 5:533-539, 1992; Muzyczka. *Current Topics in Microbiol, and Immunol.* 158:97-129, 1992; Kotin, *Human Gene Therapy* 5:793-801, 1994; Shelling and Smith *Gene Therapy* 7:165-169, 1994; and Zhou et al. *J Exp. Med.* 179:1867-1875, 1994.

Additional viral vectors useful for delivering an expression construct of the disclosure include, for example, those derived from the pox family of viruses, such as vaccinia virus and avian poxvirus or an alphavirus or a conjugate virus vector (e.g. that described in Fisher-Hoch et al., *Proc. Natl Acad. Sci. USA* 56:317-321, 1989).

Assaying Therapeutic/Prophylactic Potential of Cells and Soluble Factors

Methods for determining the ability of cells or soluble factors to treat or prevent or delay the onset or progression of a respiratory condition will be apparent to the skilled artisan.

For example, cells or soluble factors (e.g., a mixture of factors or a single factor or a fraction of factors (e.g., derived by affinity purification or chromatography)) are administered to a model of a respiratory condition and the effect on one or more symptoms is assessed.

Exemplary models of respiratory conditions include an animal model of allergy, e.g., allergic asthma, such as a model described in WO2002/098216, a mouse model of allergic asthma, e.g., induced by host dust mite protein (Fattouh et al., *Am J Respir Crit Care Med* 172: 314-321, 2005), a mouse model of severe asthma in which IL-5 and eotaxin are overexpressed, mice receiving intratracheal instillation of poly-l-lysine which are hypersensitive to methacholine when delivered as an aerosol (Homma et al., *Am J Physiol Lung Cell Mol Physiol* 289: L413-L418, 2005), bleomycin or FITC or silica induced models of pulmonary fibrosis (Muggia et al., *Cancer Treat Rev* 10: 221-243, 1983; Roberts et al., *J Pathol* 176: 309-318, 1995; Oberdorster *Inhal Toxicol* 8: 73-89, 1996).

It will be apparent to the skilled artisan from the foregoing that the present disclosure also provides a method for identifying or isolating a cell or a soluble factor for the treatment, prevention or delay of a respiratory condition, the method comprising:

(i) administering a cell or a soluble factor to a test subject suffering from a respiratory condition and assessing a symptom of the respiratory condition;
(ii) comparing the symptom of respiratory condition levels of the subject at (i) to the symptom of respiratory condition of a control subject suffering from the respiratory condition to which the cell or soluble factor has not been administered, wherein an improvement in the symptom in the test subject compared to the control subject indicates that the cell or soluble factor treats respiratory condition.

The cell may be any cell described herein according to any example.

Exemplary symptoms are described herein.

Cellular Compositions

In one example of the present disclosure STRO-1$^+$ cells and/or progeny cells thereof are administered in the form of a composition. In one example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay a respiratory condition.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

STRO-1$^+$ cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of methods of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. *J. Ped. Surg.* 23:3-9 1988; Cima, et al. *Biotechnol. Bioeng.* 38:145 1991; Vacanti, et al. *Plast. Reconstr. Surg.* 88:753-9 1991; or synthetic polymers such as polyanhydrides, polyorthoesters, and polylactic acid.

In another example, the cells may be administered in a gel scaffold (such as Gelfoam from Upjohn Company.

The cells may be administered as a component of a pharmaceutical composition specifically formulated for intranasal administration. In certain examples, the cells are co-administered with an enzyme inhibitor or an absorption enhancer. In other examples, the pharmaceutical compositions formulated for intranasal administration comprise enzyme inhibitor and/or absorption enhancers. In yet other examples, the pharmaceutical compositions comprise synthetic surfactants, bile salts, phospholipids, and cylodextrins. The cells may also be intranasally administered via an emulsion or a liposome. In certain examples, intranasal administration is achieved by use of polymeric microspheres. The cells may be administered in the presence of sodium glycohcholate (NaGC) and linoleic acid.

The pharmaceutical composition for intranasal administration may be administered as a spray, aerosol, gel, solution, emulsion, or suspension. Alternatively, the pharmaceutical composition is administered directly to the upper airways such as e.g. the paranasal sinuses. In one example, the cells or the pharmaceutical composition are administered via a microcatheter.

The cellular compositions useful for methods described herein may be administered alone or as admixtures with other cells. Cells that may be administered in conjunction with the compositions of the present disclosure include, but are not limited to, other multipotent or pluripotent cells or stem cells, or bone marrow cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of cells. Exemplary dosages are described herein. The exact amount of cells to be administered is dependent upon a variety of factors, including the age, weight, and sex of the patient, and the extent and severity of the respiratory condition.

In some examples, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near a pancreas.

In some examples of the disclosure, it may not be necessary or desirable to immunosuppress a patient prior to initiation of therapy with cellular compositions. Accordingly, transplantation with allogeneic, or even xenogeneic, STRO-1$^+$ cells or progeny thereof may be tolerated in some instances.

However, in other instances it may be desirable or appropriate to pharmacologically immunosuppress a patient prior to initiating cell therapy and/or reduce an immune response of a subject against the cellular composition. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. For example, the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Compositions of Soluble Factors

In one example, STRO-1$^+$ cell-derived and/or progeny cell-derived supernatant or soluble factors are administered in the form of a composition, e.g., comprising a suitable carrier and/or excipient. In one example, the carrier or excipient does not adversely affect the biological effect of the soluble factors or supernatant.

In one example, the composition comprises a composition of matter to stabilize a soluble factor or a component of supernatant, e.g., a protease inhibitor. In one example, the protease inhibitor is not included in an amount sufficient to have an adverse effect on a subject.

Compositions comprising STRO-1$^+$ cell-derived and/or progeny cell-derived supernatant or soluble factors may be prepared as appropriate liquid suspensions, e.g., in culture medium or in a stable carrier or a buffer solution, e.g., phosphate buffered saline. Suitable carriers are described herein above. In another example, suspensions comprising STRO-1$^+$ cell-derived and/or progeny cell-derived supernatant or soluble factors are oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the supernatant or soluble factors in the required amount in an appropriate solvent with one or a combination of ingredients described above, as required, followed by filtered sterilization.

Generally, dispersions are prepared by incorporating the supernatant or soluble factors into a sterile vehicle that contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof. In accordance with an alternative example of the disclosure, the supernatant or soluble factors may be formulated with one or more additional compounds that enhance its solubility.

Other exemplary carriers or excipients are described, for example, in Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In some cases, isotonic agents, for example, sugars, polyalcohols such as mannitol, sorbitol, or sodium chloride are included in the composition. Prolonged absorption of the injectable compositions can be brought about by including in the composition an agent which delays absorption, for example, monostearate salts and gelatin. Moreover, the soluble factors may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The supernatant or soluble factors may be administered in combination with an appropriate matrix, for instance, to provide slow release of the soluble factors.

Additional Components of Compositions

The STRO-1$^+$ cell-derived supernatant or soluble factors, STRO-1$^+$ cells or progeny thereof may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMIVCADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics.

In one example, a composition as described herein according to any example comprises an anti-inflammatory agent, an immunomodulatory agent, an immunosuppressive agent, a pain medication, or an antibiotic. In one example, the second therapeutic agent is an immunomodulatory agent. In another example, the second agent is an anti-CD3 antibody (e.g., OKT3, muronomab), an anti-IL-2 receptor antibody (e.g., basiliximab and daclizumab), an anti T cell receptor antibody (e.g., Muromonab-CD3), azathioprine, a calcineurin inhibitor, a corticosteroid, cyclosporine, methotrexate, mercaptopurine, mycophenolate mofetil, tacrolimus, or sirolimus.

Alternatively, or in addition, cells, secreted factors and/or a composition as described herein according to any example is combined with a known treatment of a respiratory condition, e.g., a steroid or LABA.

In one example, a pharmaceutical composition as described herein according to any example comprises a compound used to treat a respiratory condition. Alternatively, a method of treatment/prophylaxis as described herein according to any example of the disclosure additionally comprises administering a compound used to treat respiratory condition. Exemplary compounds are described herein and are to be taken to apply mutatis mutandis to these examples of the present disclosure.

In another example, a composition as described herein according to any example additionally comprises a factor that induces or enhances differentiation of a progenitor cell into a vascular cell. Exemplary factors include, vascular endothelial growth factor (VEGF), platelet derived growth factor (PDGF; e.g., PDGF-BB), and FGF.

In another example, a composition as described herein according to any example additionally comprises a tissue specific committed cell (TSCC). In this respect, International Patent Application No. PCT/AU2005/001445 demonstrates that administration of a TSCC and a STRO-1$^+$ cells can lead to enhanced proliferation of the TSCC. In one example, the TSCC is a vascular cell. Administration of such a composition to a subject may lead to increased production of vasculature, e.g., leading to increased nutrients being delivered to the affected tissue.

Medical Devices

The present disclosure also provides medical devices for use or when used in a method as described herein according to any example. For example, the present disclosure provides a syringe or catheter or inhaler or other suitable delivery device comprising STRO-1$^+$ cells and/or progeny cells thereof and/or soluble factors therefrom and/or a composition as described herein according to any example. Optionally, the syringe or catheter or inhaler is packaged with instructions for use in a method as described herein according to any example.

In another example, the present disclosure provides an implant comprising STRO-1$^+$ cells and/or progeny cells thereof and/or soluble factors therefrom and/or a composition as described herein according to any example. Optionally, the implant is packaged with instructions for use in a method as described herein according to any example. Suitable implants may be formed with a scaffold, e.g., as described herein above and STRO-1$^+$ cells and/or progeny cells thereof and/or soluble factors therefrom.

Modes of Administration

The STRO-1$^-$ cell-derived supernatant or soluble factors, STRO-1l cells or progeny thereof may be surgically implanted, injected, inhaled, delivered (e.g., by way of a catheter or syringe), or otherwise administered directly or indirectly to the site in need of repair or augmentation, e.g., into a lung.

In on example, the STRO-1$^+$ cell-derived supernatant or soluble factors, STRO-1$^+$ cells or progeny thereof is/are delivered to the blood stream of a subject. For example, the STRO-1$^+$ cell-derived supernatant or soluble factors, STRO-1$^+$ cells or progeny thereof are delivered parenterally. Exemplary routes of parenteral administration include, but are not limited to, intraperitoneal, intraventricular, intracerebroventricular, intrathecal, or intravenous. In one example, the STRO-1$^+$ cell-derived supernatant or soluble factors, STRO-1$^+$ cells or progeny thereof are delivered intra-arterially, into an aorta, into an atrium or ventricle of the heart or into a blood vessel, e.g., intravenously. In this regard, STRO-1$^+$ cells have been shown to migrate to sites of injury and/or to the lungs.

In the case of cell delivery to an atrium or ventricle of the heart, cells can be administered to the left atrium or ventricle to avoid complications that may arise from rapid delivery of cells to the lungs.

In one example, the STRO-1$^+$ cell-derived supernatant or soluble factors, STRO-1$^+$ cells or progeny thereof are delivered intravenously.

In one example, the STRO-1$^+$ cell-derived supernatant or soluble factors, STRO-1$^+$ cells or progeny thereof are injected into the site of delivery, e.g., using a syringe or through a catheter or a central line.

In one example, the STRO-1$^+$ cell-derived supernatant or soluble factors, STRO-1$^+$ cells or progeny thereof are delivered intranasally or by inhalation.

Selecting an administration regimen for a therapeutic formulation depends on several factors, including the serum or tissue turnover rate of the entity, the level of symptoms, and the immunogenicity of the entity. In one example, an administration regimen maximizes the amount of cells and/or factors delivered to the subject consistent with an acceptable level of side effects. Accordingly, the amount of cells and/or factors delivered depends in part on the particular entity and the severity of the condition being treated.

In one example, STRO-1$^+$ cell-derived supernatant or soluble factors, STRO-1$^+$ cells or progeny thereof are delivered as a single bolus dose. Alternatively, STRO-1$^+$ cell-derived supernatant or soluble factors, STRO-1$^+$ cells or progeny thereof are administered by continuous infusion, or by doses at intervals of, e.g., one day, one week, or 1-7 times per week. An exemplary dose protocol is one involving the maximal dose or dose frequency that avoids significant undesirable side effects. A total weekly dose depends on the type and activity of the compound/cell being used. Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects.

The present inventors have shown therapeutic benefits provided by STRO-1$^+$ cells and/or progeny thereof and/or soluble factors derived therefrom are observed for at least four weeks in a subject. Accordingly, in some examples the cells are administered weekly, fortnightly, once every three weeks or once every four weeks.

In accordance with examples of the disclosure directed to treating or delaying the progression of a respiratory condition, STRO-1$^+$ cells and/or progeny cells thereof and/or soluble factors derived therefrom are administered following diagnosis of the disorder, e.g., using standard methods known in the art and/or described herein.

For those examples directed to preventing or delaying the onset of respiratory condition, the STRO-1$^+$ cells and/or progeny cells thereof and/or soluble factors derived therefrom can administered prior to clinical diagnosis of the disorder.

In one example, a method of treatment of the disclosure comprises assessing a treated subject for improvement in one or more parameters of lung function after administration (e.g., from 7 days to 30 days afterwards), wherein the parameters of lung function are forced expiratory volume in one second (FEVI); forced volume vital capacity (FVC); FEVI/FVC; peak expiratory flow (PEF); forced expiratory flow 25%-50% or 25% 75% (average flow of air exiting the lung during the middle portion of the expiration); forced expiratory time (FET); total lung capacity (TLC); diffusing capacity, carbon monoxide (DLCO); maximum voluntary ventilation; a detectable improvement in one or more of a chest X-ray, CT scan, MRI, bronchoscopy or similar scan (e.g., visible improvement in the appearance of the lung); or a detectable improvement in the level of carbon dioxide detectable in the blood (e.g., movement of $CO_2$ levels to within a normal range). In one example, the administration results in improvement of one or more of the parameters of lung function (1) to 80% or more of expected; or (2) by at least 2%, 3%, 4%, 5%, 6%, 7%, 8%, 9%, 50%. In one example, the method comprises identifying any of the parameters that, prior to administration, are less than 80% of expected values for an individual of the same height and weight, and assessing said parameters after treatment, wherein treatment results in improvement of one or more of said parameters of lung function (1) to 80% or more of expected; or (2) by at least 2%, 3%, 4%, 5%, 6%, 7%, 8%, 9%, 50%.

The present disclosure includes the following non-limiting examples.

EXAMPLES

Example 1: Immunoselection of MPCs by Selection of STRO-3$^+$ Cells

Bone marrow (BM) is harvested from healthy normal adult volunteers (20-35 years old). Briefly, 40 ml of BM is aspirated from the posterior iliac crest into lithium-heparin anticoagulant-containing tubes.

BMMNC are prepared by density gradient separation using Lymphoprep™ (Nycomed Pharma, Oslo, Norway) as previously described (Zannettino, A. C. et al. (1998) *Blood* 92: 2613-2628). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia).

STRO-3$^+$ (or TNAP$^+$) cells were subsequently isolated by magnetic activated cell sorting as previously described (Gronthos et al. (2003) *Journal of Cell Science* 116: 1827-1835; Gronthos, S. and Simmons, P. J. (1995) *Blood* 85: 929-940). Briefly, approximately 1-3×10$^8$ BMMNC are incubated in blocking buffer, consisting of 10% (v/v) normal rabbit serum in HHF for 20 minutes on ice. The cells are incubated with 200 μl of a 10 μg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mn^{2+}$-free PBS supplemented with 1% BSA, 5 mM EDTA and 0.01% sodium azide) as above and resuspended in a final volume of 0.9 ml MACS buffer.

One hundred μl streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International Publication No. WO 2006/108229). After addition of a further 1 ml MACS buffer, the column is removed from the magnet and the TNAP$^+$ cells are isolated by positive pressure. An aliquot of cells from each fraction can be stained with streptavidin-FITC and the purity assessed by flow cytometry.

Example 2: Cells Selected by STRO-3 mAb are STRO-1$^{bright}$ Cells

Experiments were designed to confirm the potential of using STRO-3 mAb as a single reagent for isolating cells STRO-1$^{bright}$ cells.

Given that STRO-3 (IgG1) is a different isotype to that of STRO-1 (IgM), the ability of STRO-3 to identify clonogenic CFU-F was assessed by two-color FACS analysis based on its co-expression with STRO-1$^+$ cells isolated using the MACS procedure (FIG. 1). The dot plot histogram represents 5×10$^4$ events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1$^+$ cells failed to react with the STRO-3 mAb. Cells isolated by FACS from all four quadrants were subsequently assayed for the incidence of CFU-F (Table 1).

TABLE 1

Enrichment of human bone marrow cells by dual-color FACS analysis based on the co-expression of the cell surface markers STRO-1 and TNAP (refer to FIG. 1). FACS sorted cells were cultured under standard clonogenic conditions in alpha MEM supplemented with 20% FCS. The data represents the mean number of day 14 colony-forming cells (CFU-F) per 10$^5$ cells plated ± SE (n = 3 different bone marrow aspirates). These data suggest that human MPC are exclusively restricted to the TNAP positive fraction of BM which co-express the STRO-1 antigen brightly.

| Bone Marrow Fraction | Frequency of CFU-F/10$^5$ Cells | Enrichment (Fold Increase) |
|---|---|---|
| Unfractionated BMMNC | 11.0 ± 2.2 | 1.0 |
| TNAP$^+$/STRO-1$^{bright}$ | 4.511 ± 185 | 410 |
| TNAP$^+$/STRO-1$^{dull}$ | 0.0 | 0.0 |

Example 3: Therapeutic Application of Ovine MPCs in a Sheep Model of Ovine Asthma

3.1 Methods

A house dust mite (HDM) sheep model of allergic asthma was selected for studying the effect of MPCs on asthma because it uses an allergen that is clinically relevant to humans. Other models of asthma suffer from deficiencies. For example, the mouse OVA challenge model uses an allergen that is not clinically relevant to humans, the pattern and distribution of pulmonary inflammation is different from those observed in humans, both lung and panchymal inflammation/remodeling are observed and large increases in airway smooth muscle is not observed in contrast to chronic asthma in humans. Similarly, the *Ascaris* sheep model of asthma does not make use of a clinically relevant antigen and has a strong neutrophilic response together with a comparatively weak eosinophilic response to the allergen (*ascaris suum*) not normally exposed in humans.

Asthma was initiated in sheep by administration of three subcutaneous injections of house dust mite antigen (50 µg) with alum two weeks apart. Sheep showing high IgE responses as detected by ELISA were then selected, with a 1.5-fold increase in IgE levels following antigen administration considered a "high IgE response".

On days 7, 28 and 49 sheep received aerosol challenges with house dust mite antigen (5 mL containing 200 µg/mL antigen) using a nebulizer connected to a mechanical ventilator. The mechanical ventilator assists the sheep to breathe for 10 minutes at 20 breaths per minute so that each sheep received a dose of 200 breaths of aerosolized antigen per challenge. This challenge has been previously shown to be sufficient to induce asthmatic and inflammatory responses in sheep.

On days 7, 28 and 49 bronchial hyperresponsiveness was quantitated by calculating the dose-response to increasing concentrations of the brochoconstrictor carbachol. The expected dose range for this test is between 5-300 breaths of 1 mg/ml aerosilized carbachol to give a 100% increase in resistance.

Early phase asthmatic responses were also measured, with the expected range of responses being between 50% and 900% change in resistance after antigen administration compared with baseline (pre-antigen administration) values.

Figure 3:
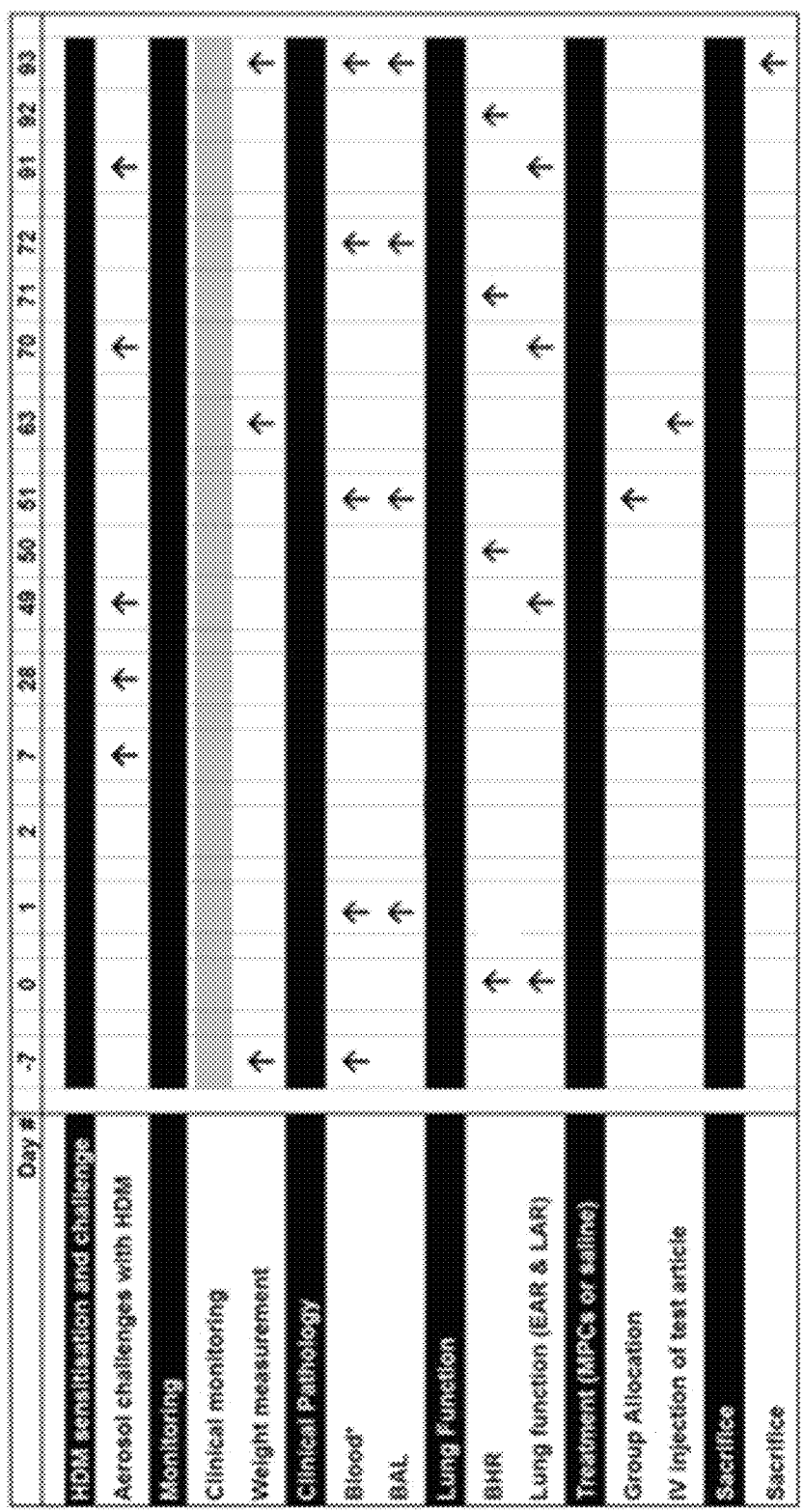
FIG. 3 is a diagrammatic representation of the timeline of the study to assess the safety and efficacy of MPCs in treating a sheep model of asthma.

Sheep were then randomized into four groups as shown in Table 2, such that all groups contain sheep with a similar range of physiological responses. Ovine MPCs (passage 5) in ProFreeze™/DMSO/αMEM were diluted in saline and then administered to the relevant groups on day 63 (two weeks after the administration of the third aerosol challenge of antigen). A summary of the treatment protocol is shown in FIG. 3.

TABLE 2

| Treatment groups | | | |
|---|---|---|---|
| | | Treatment | |
| Group | No of animals | Type | Dose |
| A | 10 | House dust mite allergen and MPCs | 25 million MPCs |
| B | 11 | House dust mite allergen and MPCs | 75 million MPCs |
| C | 10 | House dust mite allergen and MPCs | 150 million MPCs |
| D | 11 | House dust mite allergen and saline (control) | N/A |

Ovine MPCs were administered by intravenous infusion (100 mL/30 minutes) into the jugular vein. Sheep were then challenged again one and four weeks (days 70 and 91, respectively) with house dust mite allergen.

The measurement of baseline lung function (early asthmatic response [EAR]) was performed by assessing esophageal and tracheal pressures and pulmonary airflows to calculate airway resistance, as previously described by Koumoundouros et al., Exp. Lung Res., 32: 321-330, 2006. In this protocol, a balloon catheter was inserted nasally into the lower esophagus to measure esophageal pressure (i.e. external pressure). To measure internal airway pressure, a tracheal catheter was placed in a nasally inserted endotracheal tube. Airflow was measured via a pneumotachograph (Hans Rudolph, Kansas City, USA) attached to the proximal end of the endotracheal tube. The esophageal and tracheal catheters, and pneumotachograph were connected to differential transducers which allow the measurement of transpulmonary pressure together with airflow. Digital data from these recordings were analyzed in a customized Labview Pty Ltd software program, to record airway resistance on a breath-by-breath basis. Allergen-induced bronchoconstriction was measured in sheep by analyzing airway resistance changes at specific times after an aerosol challenge with HDM. Resistance values were recorded for one hour immediately after this challenge, to assess the early phase asthmatic response (EAR), then rerecorded 6 hours after challenge to assess the 6 hour asthmatic responses. The results for EAR are expressed as the percentage change in airway resistance from baseline resistance values after an aerosolized saline challenge to peak resistance values over the first hour after HDM challenge. The LAR data are expressed as the percentage change in airway resistance from baseline resistance values to average resistance values measured six hour after HDM challenge.

Bronchial hyperresponsiveness (BHR), also called airway hyperresponsiveness (AHR), is a measure of the reactivity of airway closure in response to a non-specific stimulant. Asthmatic airways are notoriously twitchy, and react to relatively low doses of bronchoconstricting agents such as the cholinergic agonists carbachol and methacholine. In sheep, BHR was assessed before the start of the HDM challenge period, and then after several weeks of HDM challenges. This was achieved by administering the bronchoconstrictor carbachol in a range of doubling aerosol doses (0.25%-4% w/v carbachol) and measuring changes in airway resistance immediately after each dose of carbachol. The results were expressed as the concentration of carbachol aerosol needed to increase airway resistance by 100% from baseline or the maximum dose of carbicol has been reached. The concentration of the administered carbachol dose was measured in Breath Units (BUs); one BU is one breath of 1% w/v carbachol. Sheep that have been sensitized in the lungs to HDM usually bronchoconstrict with relatively low doses of carbachol.

Approximately 20-30 mL of blood was collected on Day −7 (study entry baseline) and 24 h after BHR testing (Days 2, 51, 72, 93) and the following assays performed:

Hematology and Coagulation: red blood cell count (RBC), white blood cell count (WBC), hemoglobin (Hb), hematocrit, platelets, neutrophils, lymphocytes, monocytes, eosinophils, basophils, fibrinogen.

Biochemistry: sodium, potassium, chloride, bicarbonate, glucose, creatinine, calcium, magnesium, phosphate, total protein, albumin, total bilirubin, aspartate transaminase (AST), alanine transaminase (ALT), gamma-glutamyl transpeptidase (GGT).

Cytokine testing: Cytokines (TNF-α and IFN-γ)

Serum samples collected at Day 49, Day 63, and Day 91 were assayed for the presence of IgE by standard enzyme-linked immunosorbent assay (ELISA).

Broncho-alveolar lavage (BAL) cells were collected by infusing 10 mL saline into the left lung using a fiber-optic bronchoscope and recovering BAL cells and fluid.

BAL cells were differentially stained with Haem Kwik (HD Scientific Pty Ltd.) stain to ascertain the percentages of the various leukocytes present. BAL was performed on Day −7 (study entry baseline) and 24 h after BHR testing (Days 2, 51, 72, 93).

Animals were euthanized using an overdose of pentobarbitone sodium (at least 200 mg/kg; i.e. 20 mL of a 400 mg/mL solution per 40 kg sheep.

Necropsy and tissue collection are performed on all animals that die or are euthanized.

Tissue samples were collected at necropsy (Day 93) from the left caudal lung field, and frozen in OCT embedding medium in molds on aluminium trays floating on liquid nitrogen for immunohistochemistry. Two tissue blocks were frozen per sheep lung. Frozen sections (5 μm) were stained using mAbs against the sheep cell surface molecules CD4, CD8, CD45R, γδ, and IgE. Eosinophils were identified after tissue staining with endogenous peroxidase and counterstained with hematoxylin and eosin-γ.

Individual cells were examined and counted in the parenchyma, airway lamina propria, and outer airway wall for each sheep, and expressed as the number of cells per $mm^2$ of tissue examined. For high density cell types, at least one hundred cells were counted in the respective areas, at 200 times magnification, to ascertain the cell density. For low density cell types, the density was calculated from nonoverlapping fields taken from the all the relevant areas from the complete section. All cell identification, counting, and density calculations were performed by observers who were blinded to the treatment groups.

3.2 Results

Figure 4:
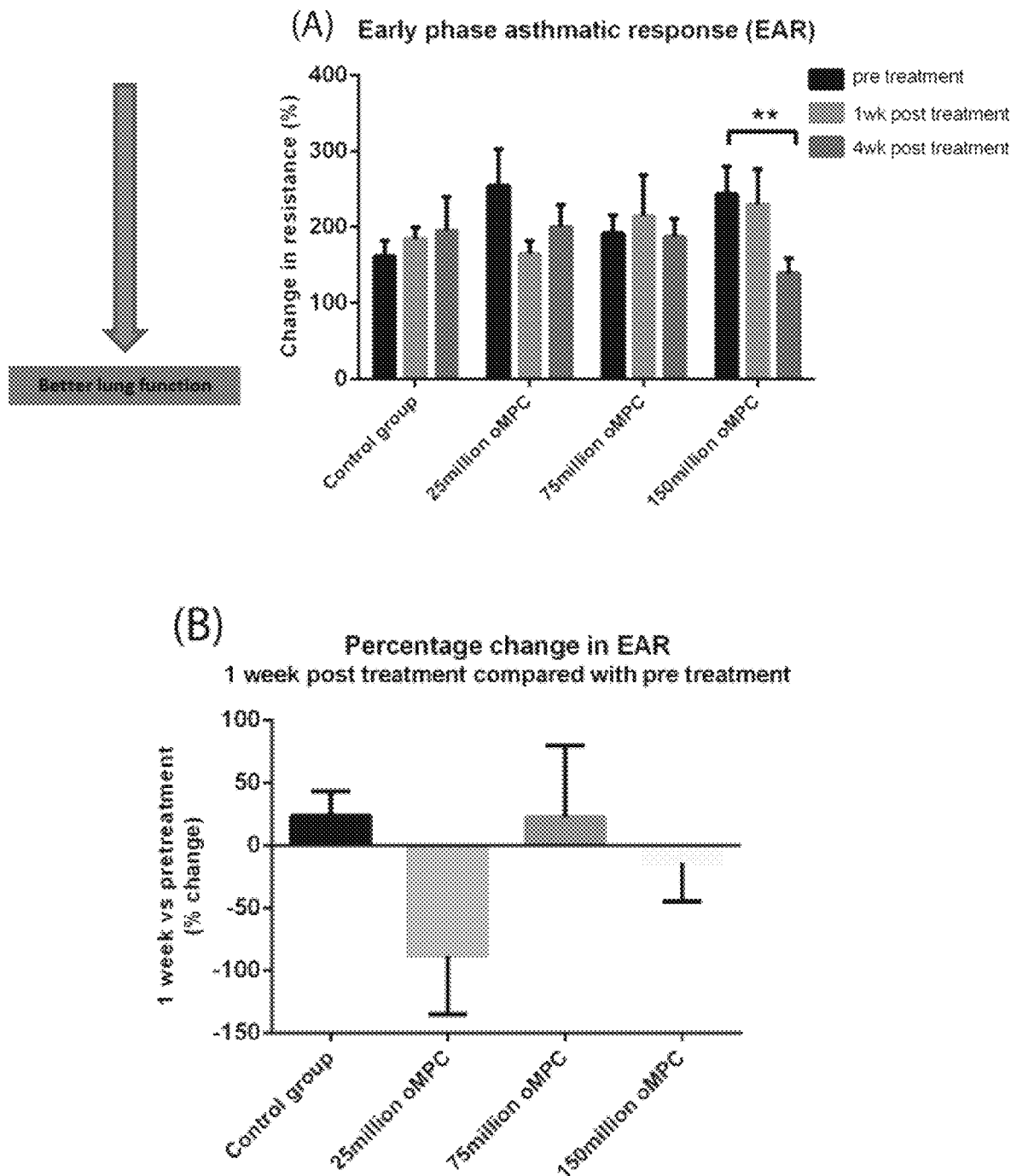
FIG. 4 is a series of graphical representations showing early-phase asthmatic response (EAR) over the course of the study for saline and MPC treatment groups. Summary EAR data are shown in (A) for the control group, and the three treatment groups, 25 million, 75 million, and 150 million oMPCs. The data represents the percentage change in resistance from baseline resistance readings taken after control saline aerosolized challenge to peak resistance readings taken over the first hour after allergen challenge. The EAR readings were taken on three occasions throughout the trial: 2 weeks before oMPC/saline treatment (pretreatment); 1 week after oMPC/saline treatment (1 wk post treatment); and 4 weeks after oMPC/saline treatments (4 wk post treatment). The data in (B) and (C) show comparisons between the control and treatment groups for the percentage change in EAR from pretreatment to 1 week, and 4 weeks, after treatments respectively. Data is presented as Mean±SEM. N=11 for control group and 75 million oMPC group; N=10 for 25 million and 150 million oMPC group. **$p<0.01$ *$p<0.05$.
Figure 4:
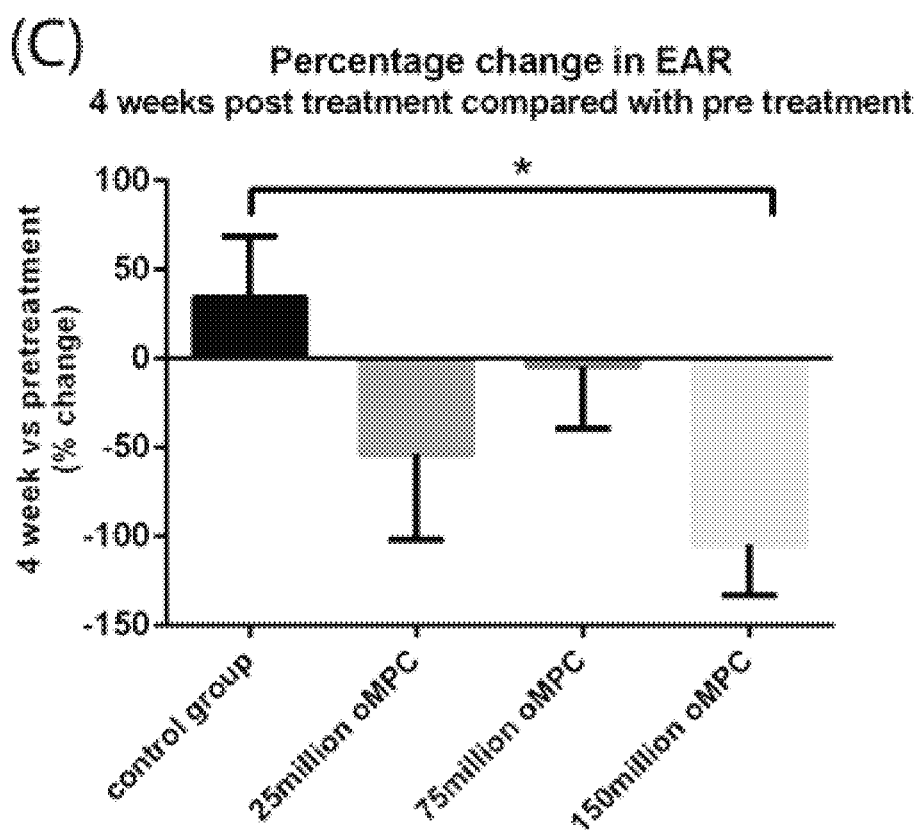

Early Phase Asthmatic Response (EAR) in HDM-Sensitized Asthmatic Sheep at Pre-Treatment, 1 and 4 Weeks after a Single Intravenous Infusion of oMPC or Saline Sheep which received 150 million oMPCs had significantly improved lung function during the hour after allergen challenge at the 4 week post oMPC treatment time point (FIGS. 4A, B & C). The improvement in lung function at the 4 week post oMPC treatment time point manifested as a 57.1% reduction in EAR after allergen challenge when compared to pre-oMPC treatment EAR ($p<0.05$ (FIGS. 4A & C).

Figure 5:
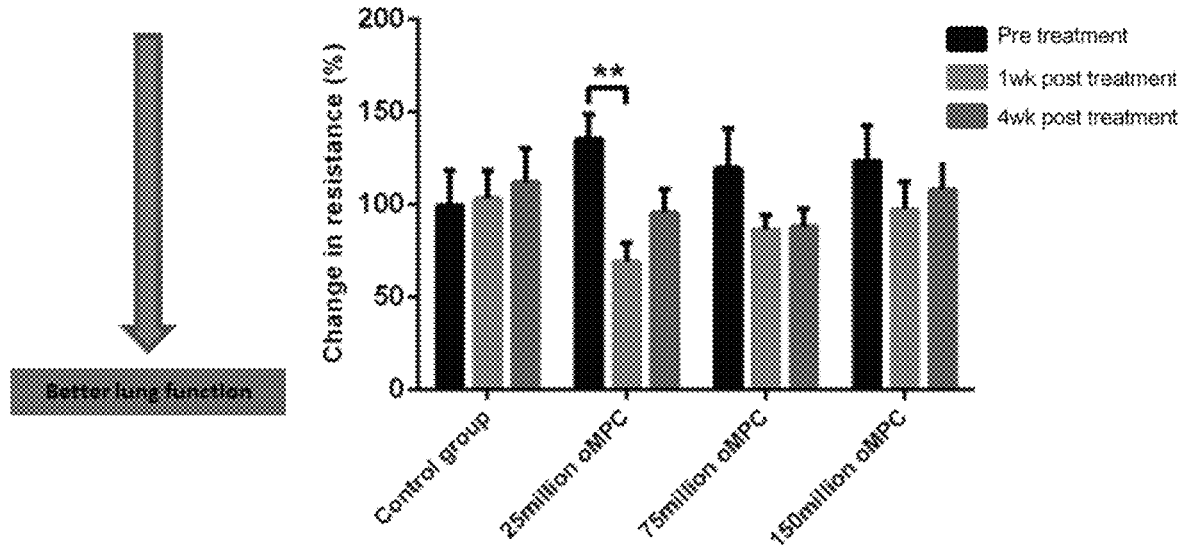
FIG. 5 is series of graphical representations showing late phase asthmatic response (LAR) over the course of the study for saline and MPC treatment groups. Summary LAR data are shown in (A) for the control group, and the three treatment groups, 25 million, 75 million, and 150 million oMPCs. The data represents the percentage change in resistance from baseline resistance readings taken before aerosolized allergen challenge to resistance readings taken 6 hours after allergen challenge. The LAR readings were taken on three occasions throughout the trial: 2 weeks before oMPC/saline treatment (pretreatment); 1 week after oMPC/saline treatment (1 wk post treatment); and 4 weeks after oMPC/saline treatments (4 wk post treatment). The data in (B) and (C) show comparisons between the control and treatment groups for the percentage change in LAR from pretreatment to 1 week, and 4 weeks, after treatments respectively. Data is presented as Mean±SEM. N=11 for control group and 75 million oMPC group; N=10 for 25 million and 150 million oMPC group. **$p<0.01$ *$p<0.05$
Figure 5:
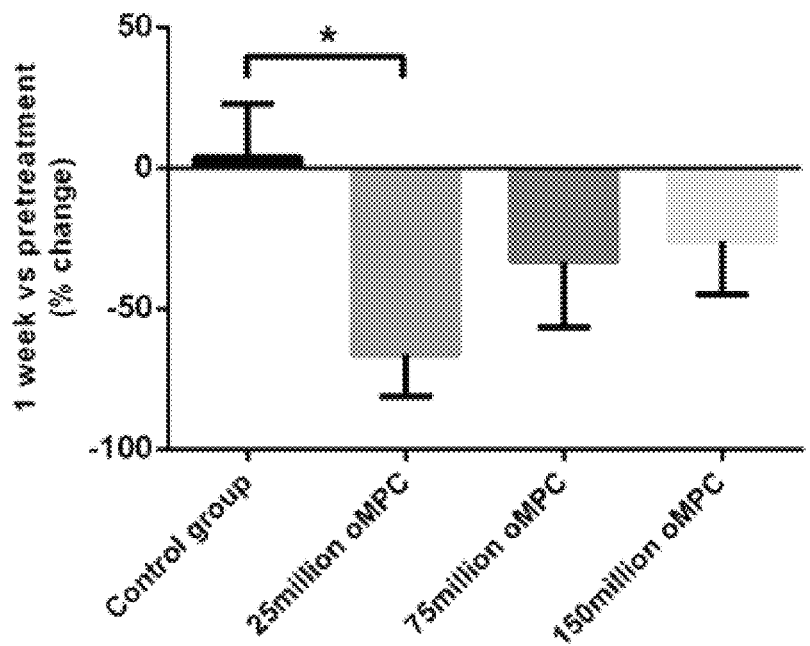
Figure 5:
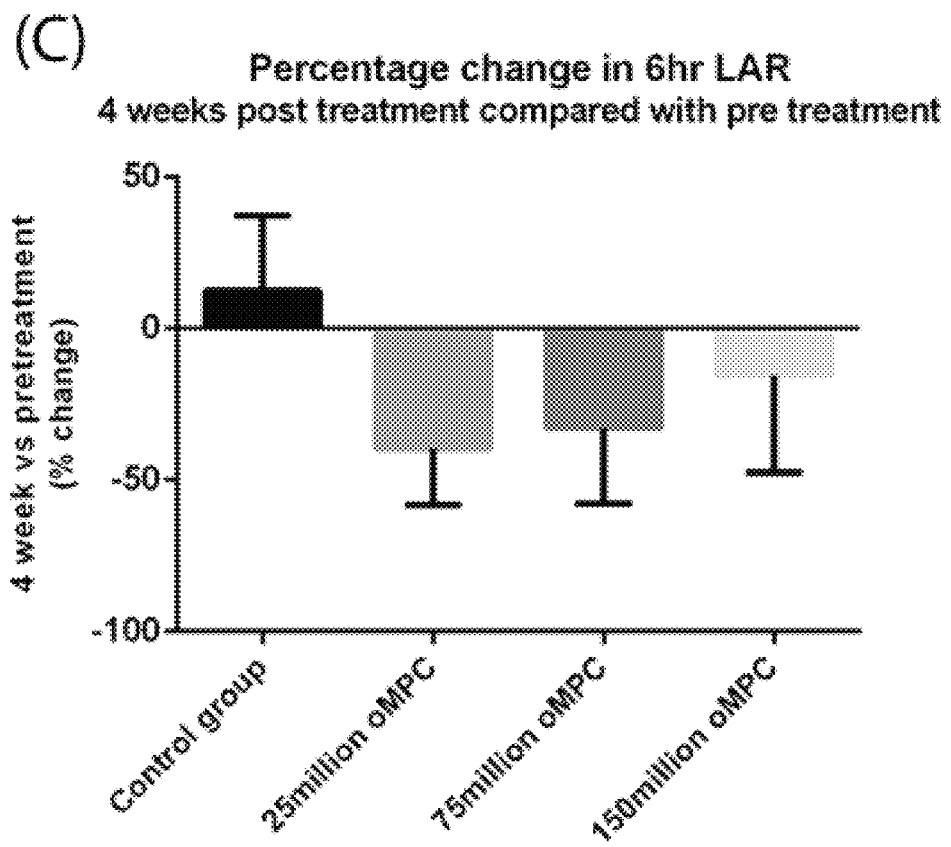

Late Phase Asthmatic Response (LAR) in HDM-Sensitized Asthmatic Sheep at Pre-Treatment, 1 and 4 Weeks after a Single Intravenous Infusion of oMPC or Saline The saline control group showed a trend toward increase in LAR at six hours after allergen challenge when assessed at both the 1 week and 4 week time points when compared to pretreatment values (FIG. 5A). The 25 million oMPC treatment group was associated with a significant decline in 6 hour LAR at the 1 week when compared to pretreatment values (FIG. 5A). The 75 and 150 million oMPC treatment groups all experienced a trend towards a decline in 6 hour LAR at both the 1 and 4 week post-treatment time points when compared to pretreatment values. A summary graph showing the comparative changes between the treatment groups in the 6 hour LAR is shown in FIG. 5B. When evaluating the relative change in LAR by a percent change from pre-treatment to follow-up treatment, the percentage change in LAR in the 25 million oMPC dose group was significantly improved compared to control at the 1 week time point ($p<0.05$, FIG. 5B). Similar trends were shown for the 6 hour LAR at the 4 week post oMPC treatment time point (FIG. 5C).

Figure 6:
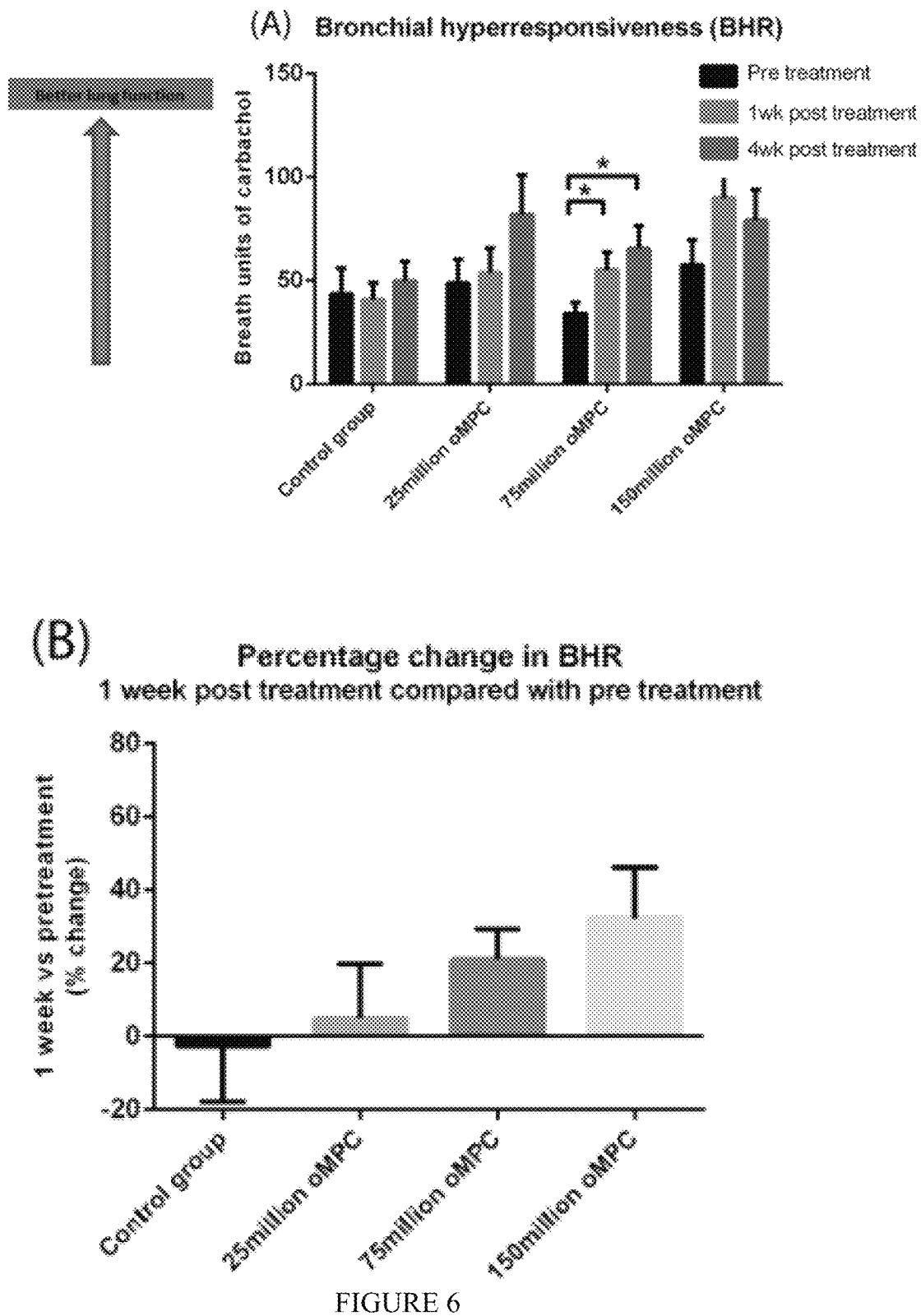
FIG. 6 is a series of graphical representations showing bronchial hyperresponsiveness (BHR) over the course of the study for saline and MPC treatment groups. Summary BHR data are shown in (A) for the control group, and the three treatment groups, 25 million, 75 million, and 150 million oMPCs. The BHR data on the y axis represents the mean number of breath units of carbachol required to induce a 100% change in resistance. The BHR readings were taken on three occasions throughout the trial: 2 weeks before oMPC/saline treatment (pretreatment); 1 week after oMPC/saline treatment (1 wk post treatment); and 4 weeks after oMPC/saline treatments (4 wk post treatment). The data in (B) and (C) show comparisons between the control and treatment groups for the percentage change in BHR from pretreatment to 1 week, and 4 weeks, after treatments respectively. Data in (D) shows BHR data comparisons between the control group and pooled treatment groups. Data is presented as Mean±SEM. N=11 for control group and 75 million oMPC group; N=10 for 25 million and 150 million oMPC group. *$p<0.05$ **$p<0.01$
Figure 6:
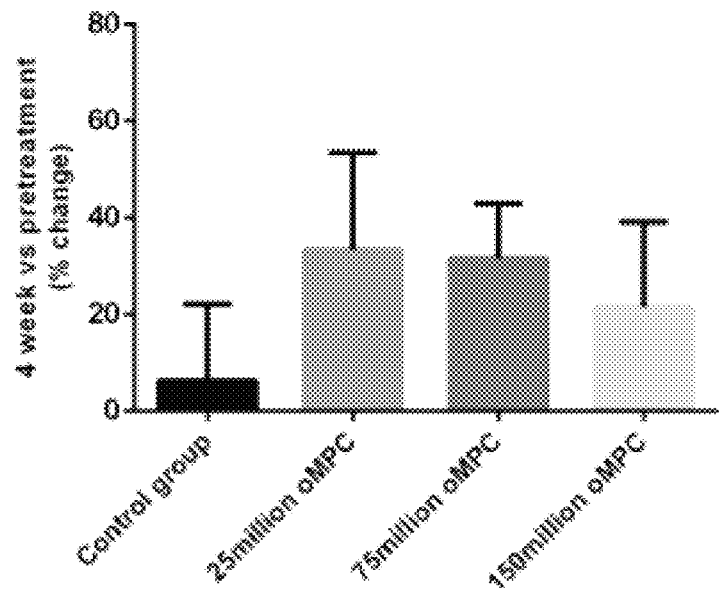
Figure 6:
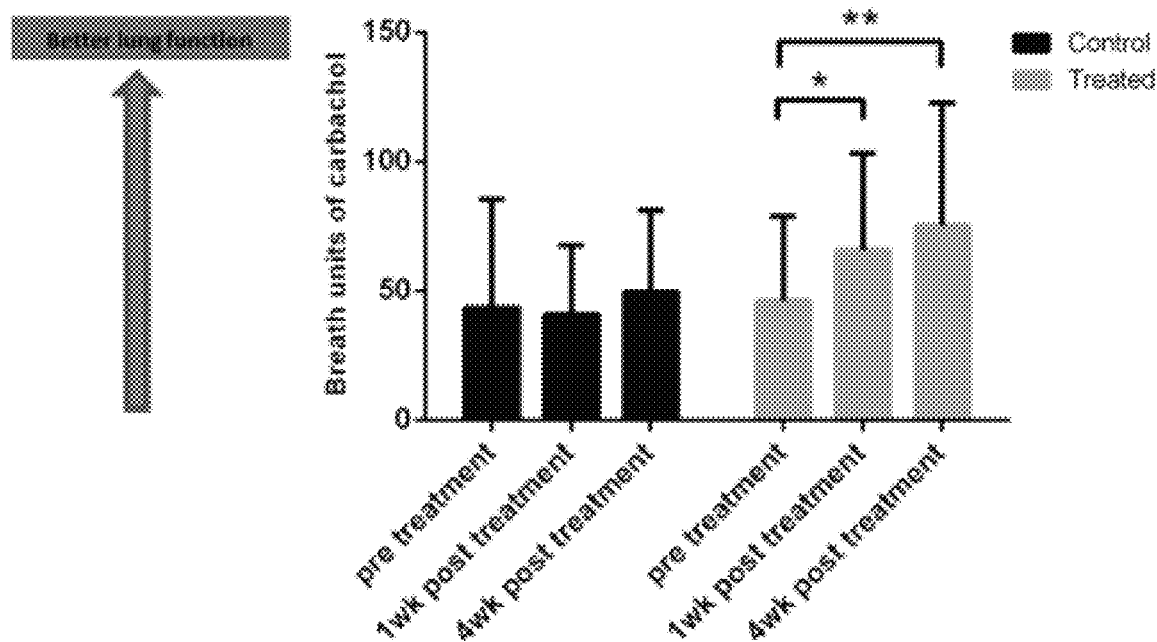

Bronchial Hyperresponsiveness (BHR) in Asthmatic Sheep at Pre-Treatment, 1 and 4 Weeks after a Single Intravenous Infusion of oMPC or Saline The control group which received saline vehicle treatment in lieu of oMPCs experienced no significant changes in BHR at the 1 week and 4 week time points (FIGS. 6A, B, C & D). The sheep group which received 75 million oMPCs had significantly improved BHR indices at both the 1 and 4 week time points post oMPC treatment when compared with BHR measured before oMPC treatment (FIG. 6A). The differences between the pre treatment and 1 and 4 week time points were statistically significant when all treatment groups were pooled together in a post hoc analysis (FIG. 6D).

Figure 7:
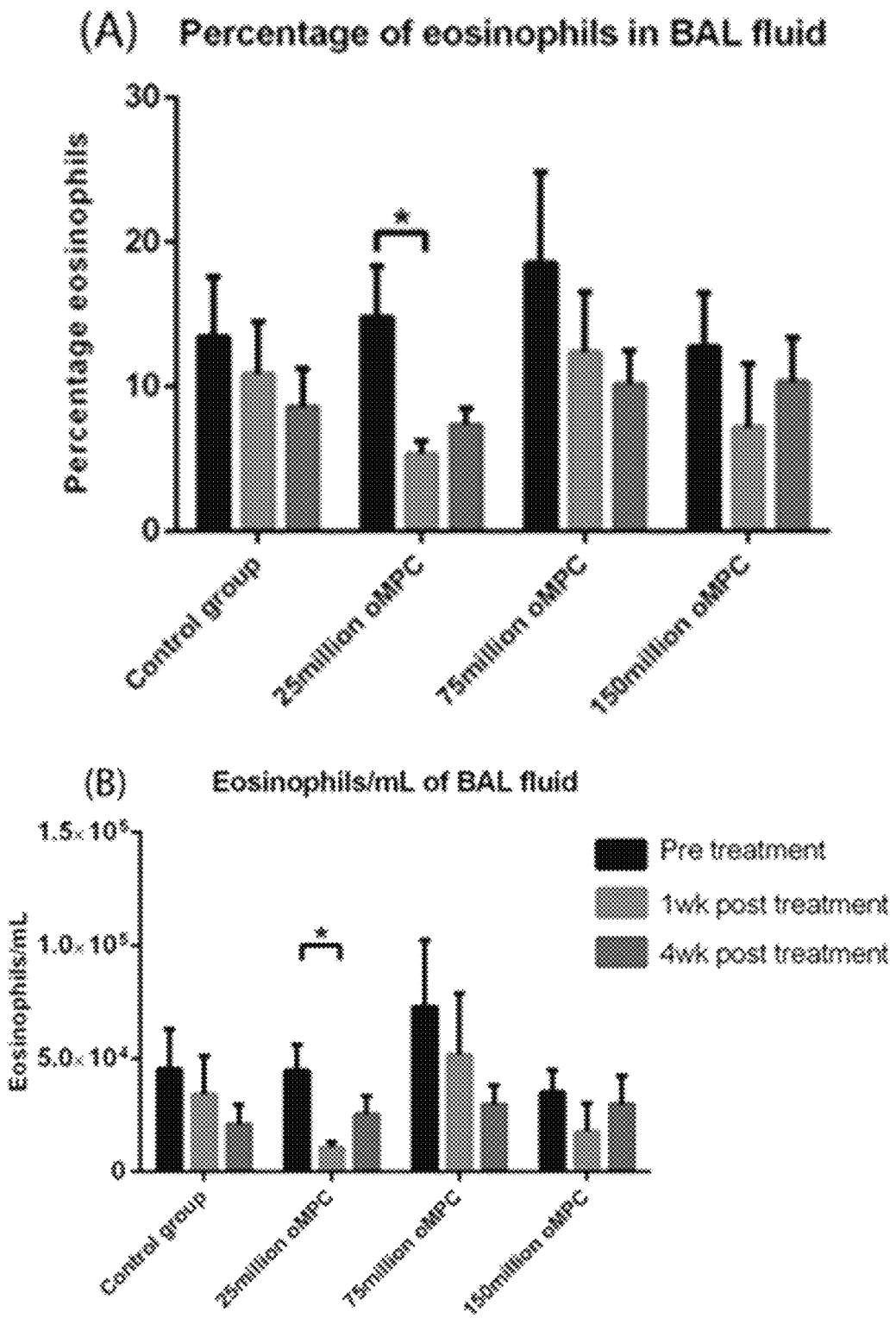
FIG. 7 is a series of graphical representations showing eosinophils in bronchoalveolar (BAL) fluid over the course of the study for saline and MPC treatment groups. Data are presented as a summary of percentage eosinophils (A), change in percentage eosinophils from pre-treatment at 1 week (C) and 4 weeks (D) post treatment, and control group compared to pooled treatment groups (E). Eosinophils/mL are shown in (B). Data is presented as Mean±SEM. N=1 for control group and 75 million oMPC group; N=10 for 25 million and 150 million oMPC group. *$p<0.05$, **$p<0.0^1$.
Figure 7:
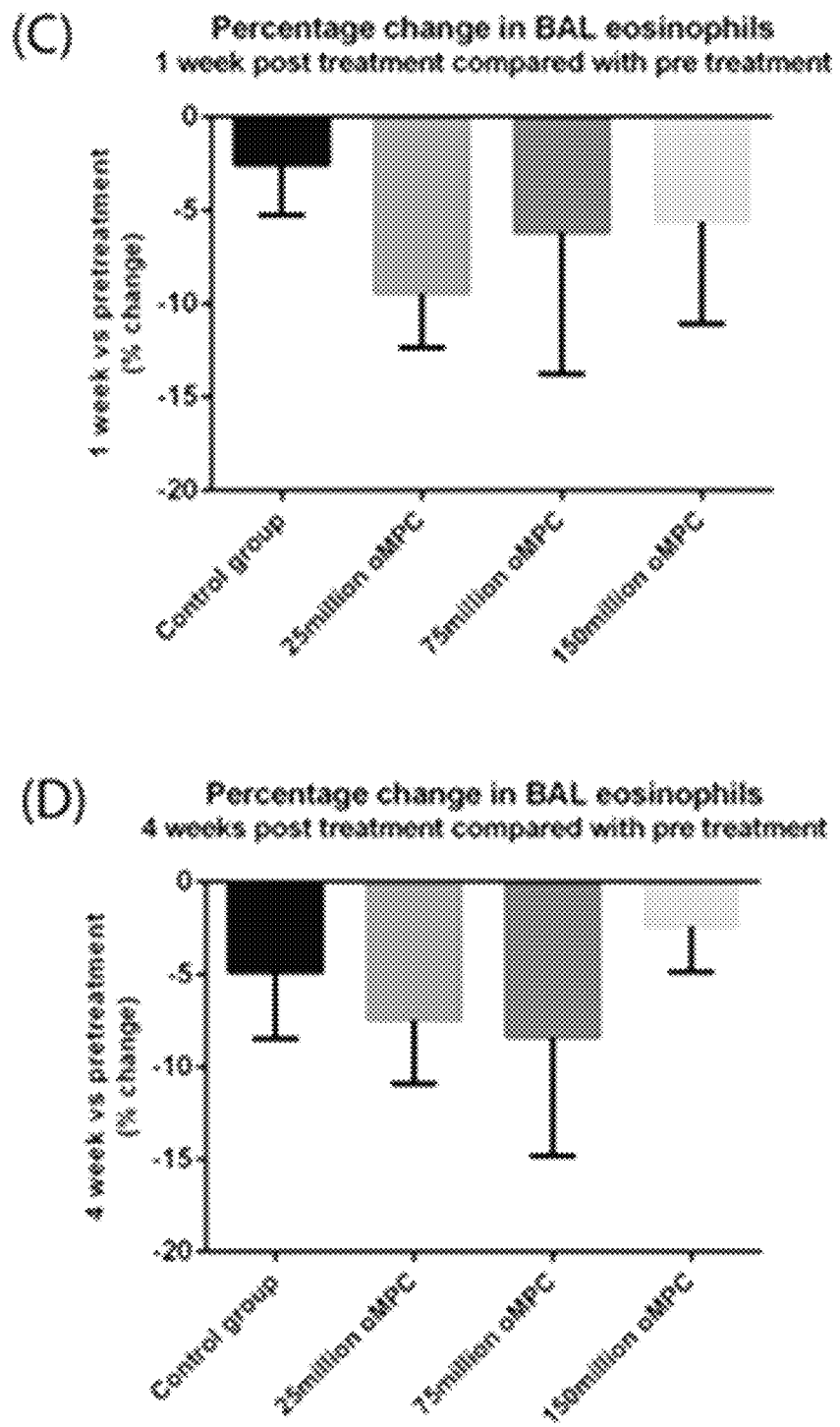
Figure 7:
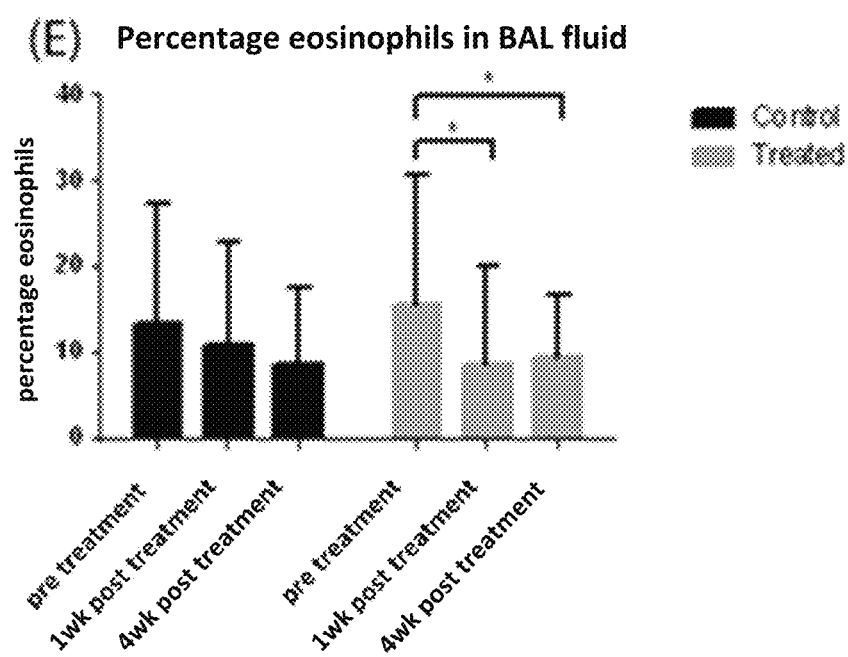

Bronchoalveolar Lavage (BAL) Fluid Analysis: Inflammatory Cell Profile in BAL Fluid in Asthmatic Sheep at Pre-Treatment, 1 and 4 Weeks after a Single Intravenous Infusion of oMPC or Saline Bronchoalveolar lavage (BAL) was sampled two days after allergen challenge at 1 week and 4 weeks after either oMPC or saline-control treatment. In all sheep used in this trial the mean baseline percentage of eosinophils of total BAL cells sampled before allergen challenge and stem cell treatment is 4.5%. The mean percentage of eosinophils in the BAL of all sheep sampled 2 days after allergen challenges and before stem cell or saline treatments (i.e. mean pretreatment percentage of BAL eosinophils) is 15.0%. Analysis of eosinophils in the BAL fluid recovered from trial sheep 2 days after an allergen challenge and post oMPC treatment revealed that there was a significant difference between the pre-treatment and 1 week time points for sheep infused with 25 million oMPCs (FIGS. 7A & B). For the 75 million and 150 million oMPC treated groups, the differences in eosinophil numbers in the BAL fluid between pretreatment and the 1 and 4 week time points did not reach statistical significance. However, the differences between the pre- and post-treatment BAL eosinophils at both the 1 and 4 week time points were statistical significant when all three treatment values were pooled in a post hoc analysis (FIG. 7E).

Figure 8:
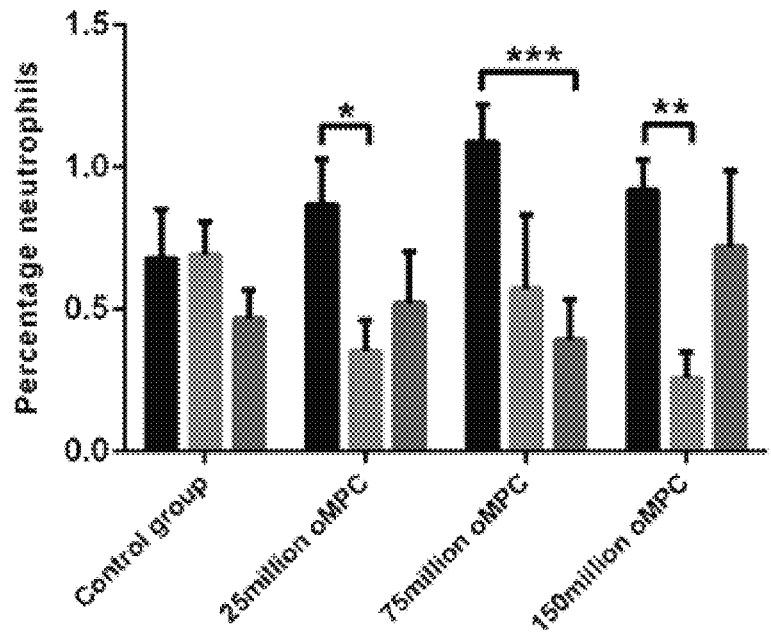
FIG. 8 is a series of graphical representations showing neutrophils in bronchoalveolar (BAL) fluid over the course of the study for saline and MPC treatment groups. Data is presented as a summary of percentage neutrophils (A), and neutrophils/mL (B). Data is presented as Mean±SEM. N=1 for control group and 75 million oMPC group; N=10 for 25 million and 150 million oMPC group. *$p<0.05$, $p<0.01$, * $p<0.005$
Figure 8:
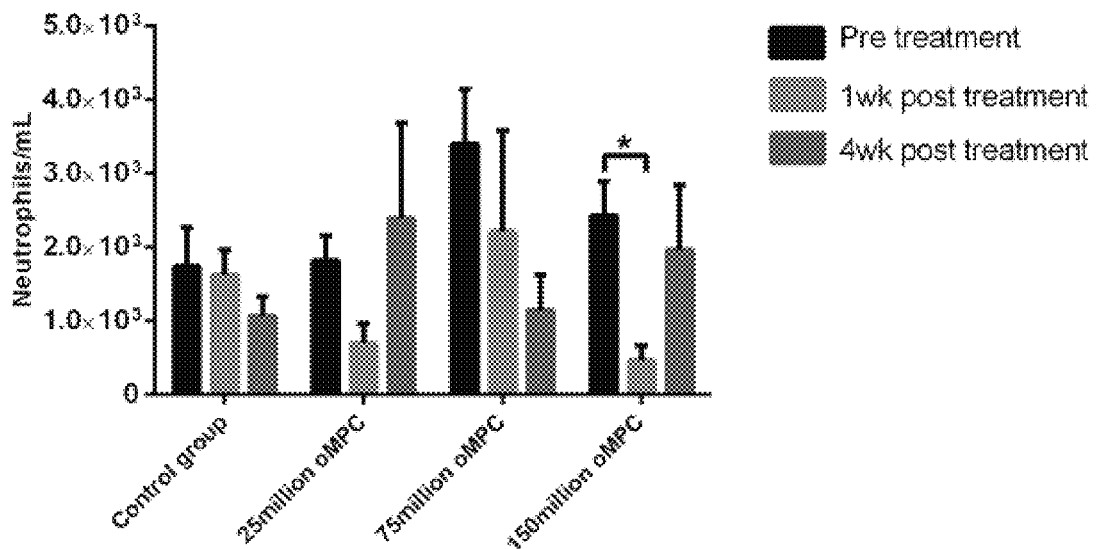

In all sheep used in this trial the mean percentage of neutrophils of total BAL cells sampled two days after allergen challenge, and before stem cell or saline treatments, is a relatively low 0.89%. The percentages of neutrophils in the BAL fluid were significantly lower at the 1 week time point post oMPC, compared to pretreatment values, for the 25 and 150 million oMPC treated sheep (FIG. 8A). For the 75 million oMPC group, the percentages of neutrophils in the BAL fluid were significantly lower at the 4 week post oMPC time point, compared to pretreatment values (FIG. 8A).

Figure 9:
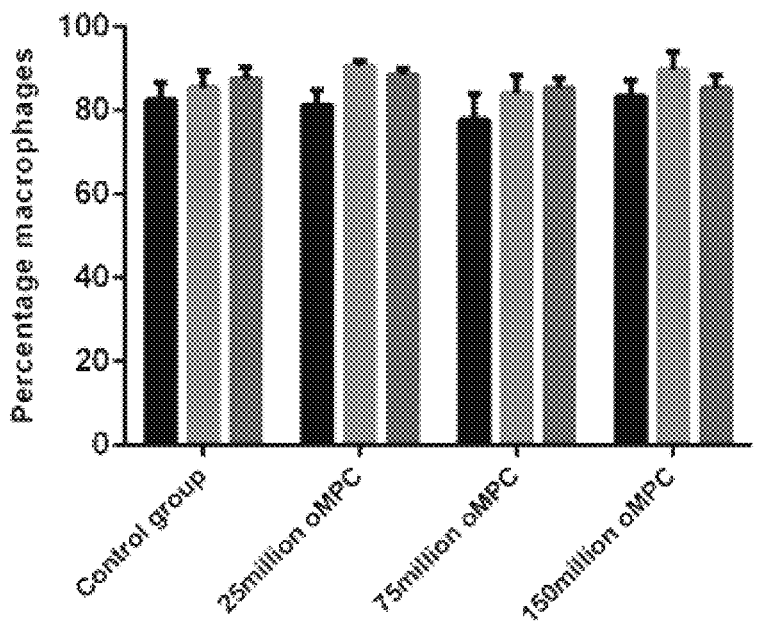
FIG. 9 is a series of graphical representations showing macrophages in bronchoalveolar (BAL) fluid over the course of the study for saline and MPC treatment groups. Data is presented as a summary of percentage macrophages (A), and macrophages/mL (B). Data is presented as Mean±SEM. N=1 for control group and 75 million oMPC group; N=10 for 25 million and 150 million oMPC group.
Figure 9:
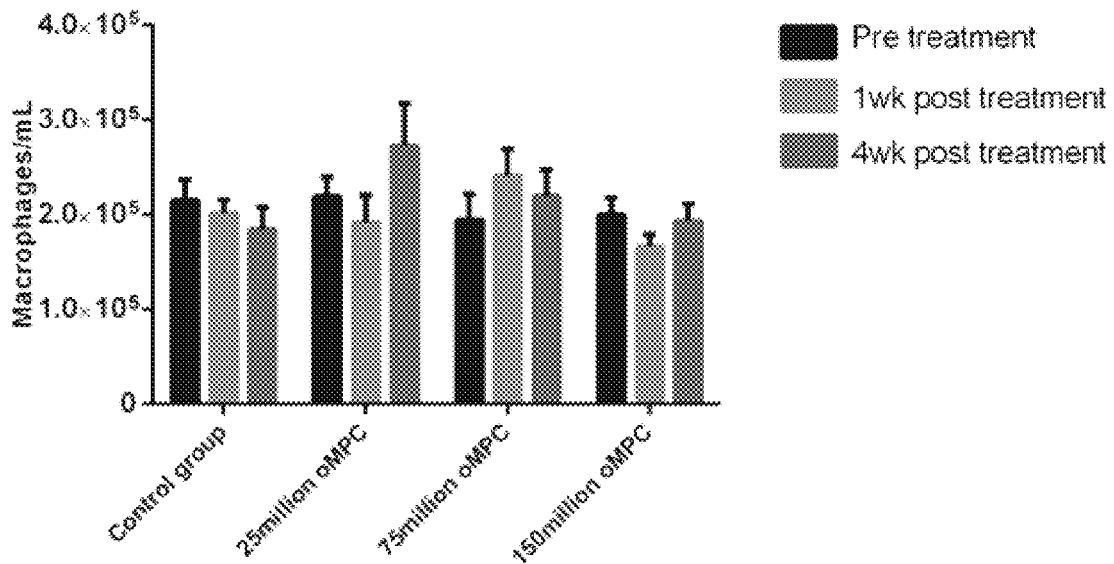
Figure 10:
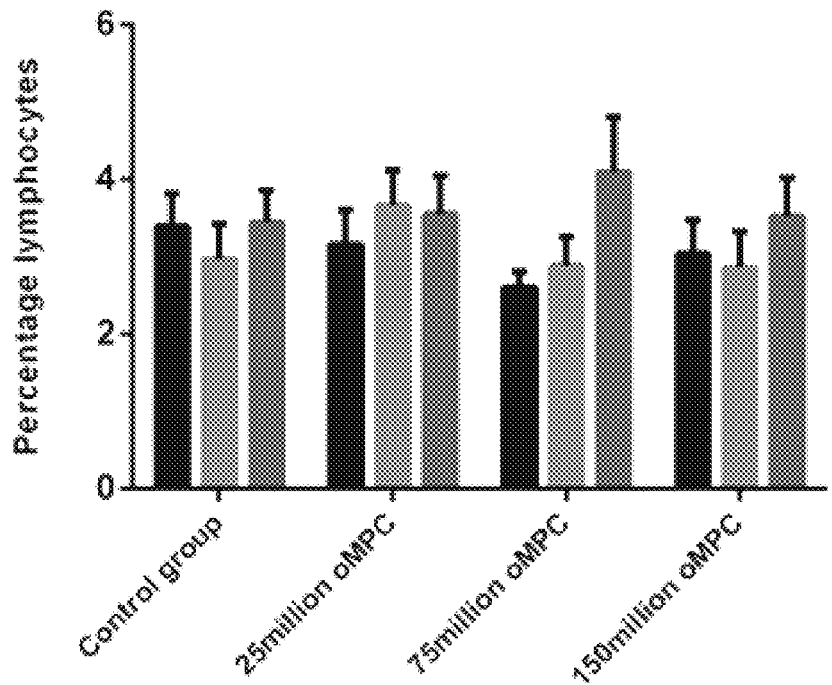
FIG. 10 is a series of graphical representations showing lymphocytes in bronchoalveolar (BAL) fluid over the course of the study for saline and MPC treatment groups. Data are presented as a summary of percentage lymphocytes (A), and lymphocytes/mL (B). Data is presented as Mean±SEM. N=1 for control group and 75 million oMPC group; N=10 for 25 million and 150 million oMPC group.
Figure 10:
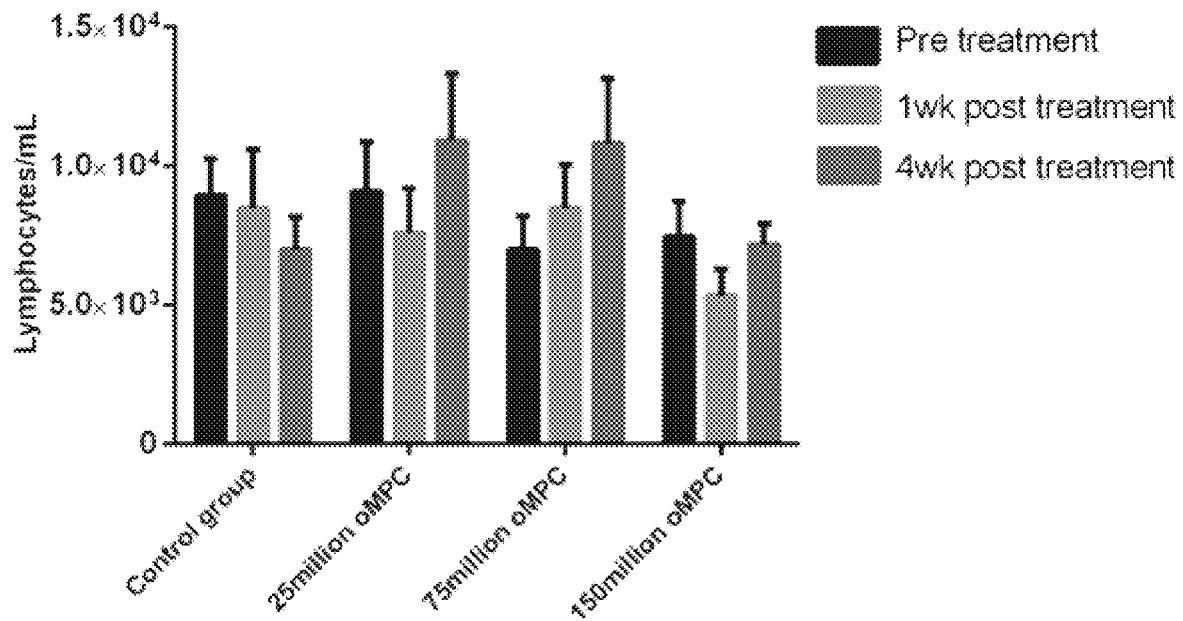

Cytospot analysis of lymphocytes and macrophages in the BAL fluid recovered from all trial sheep 2 days after an allergen challenge revealed that there were no significant differences between the groups for any of these cell types in BAL fluid (FIGS. 9-10).

Figure 11:
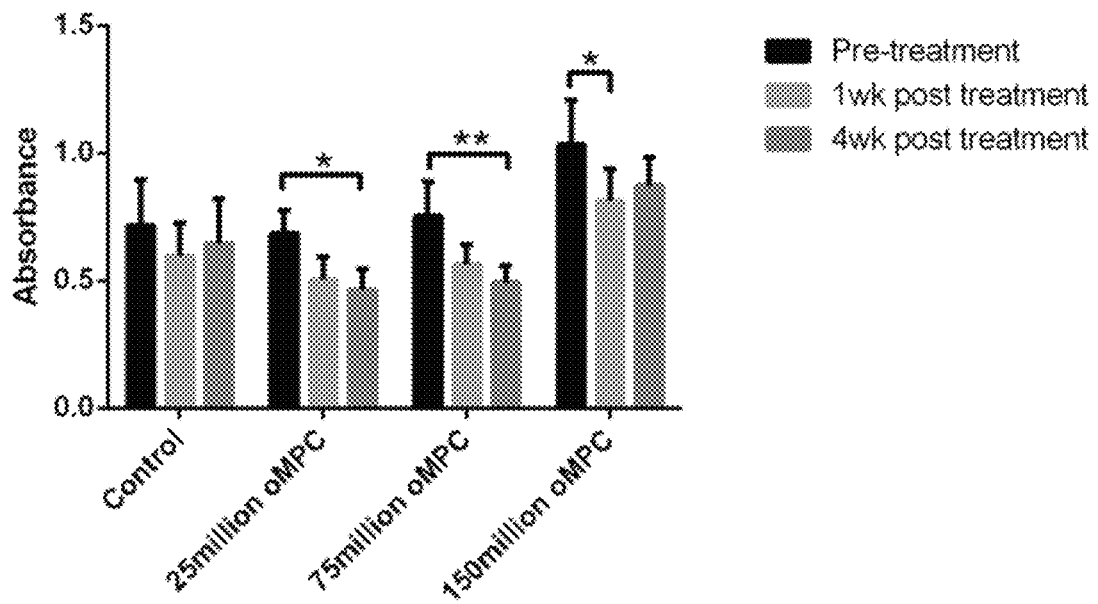
FIG. 11 is a series of graphical representations showing IgE levels in sera of asthmatic sheep. ELISA data showing mean absorbance (Abs) levels for HDM-specific IgE in the sera of trial sheep. Data is presented as mean±SEM and show comparisons of HDM-IgE levels before and after oMPC treatments (A), and the percentage change in IgE levels from pre-treatment at 1 week (B) and 4 weeks (C). Pretreatment, 1 wk post-treatment, and 4 week post-treatment sera were taken from all sheep on trial days 51, 72 and 93 respectively. N=11 for control group and 75 million oMPC group; N=10 for 25 million and 150 million oMPC groups. *$p<0.05$ **$p<0.01$.
Figure 11:
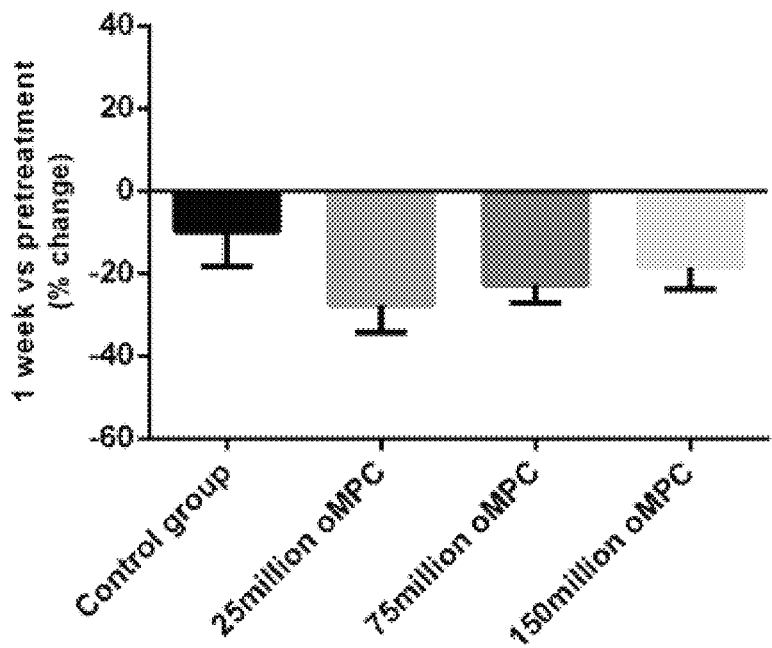
Figure 11:
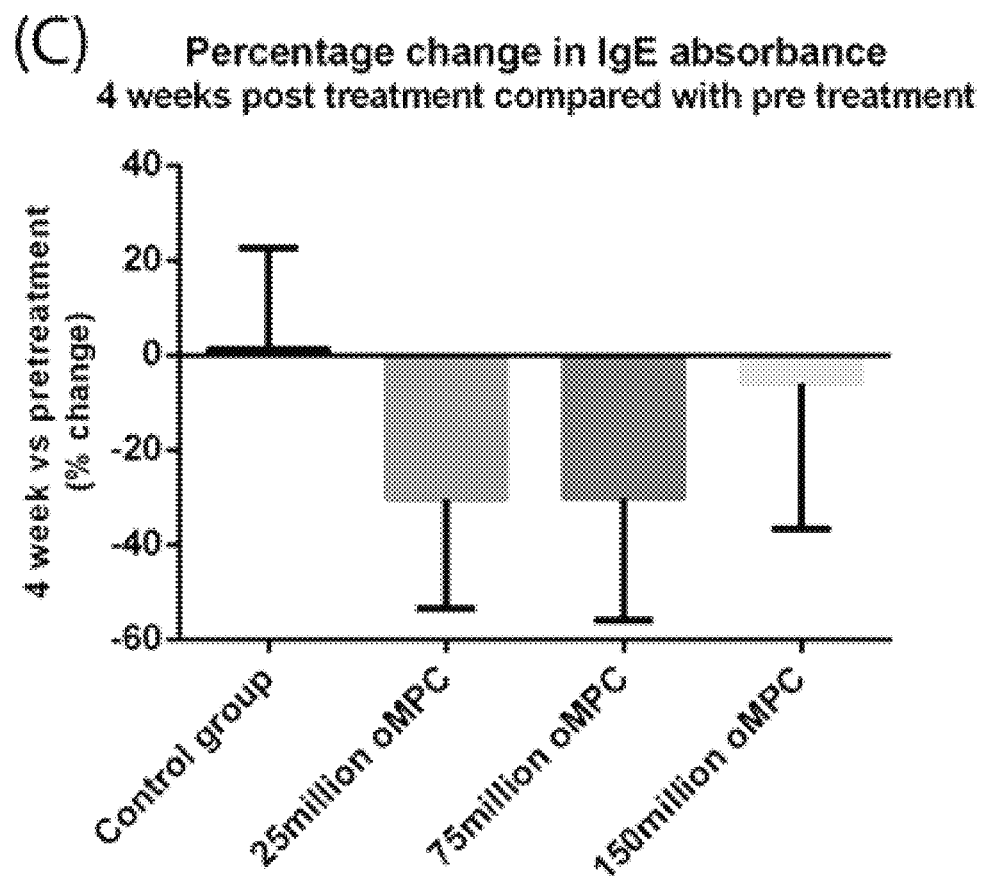

HDM-Specific IgE in Sera of Asthmatic Sheep at Pre-Treatment, 1 and 4 Weeks after a Single Intravenous Infusion of oMPC or Saline Since allergen-induced asthma is associated with allergen-specific IgE, the levels for circulating HDM-specific IgE in the sera of all sheep were assessed before oMPC administration, and at two time points after, oMPC treatments at weeks 1 and 4 (FIG. 11A). The results show that the 150 million oMPC dose of was effective in significantly reducing HDM-specific IgE 1 week after oMPC treatment compared with pretreatment levels of HDM-specific IgE (FIG. 11A). The 25 and 75 million oMPC treatments significantly reduced the HDM-specific IgE 4 weeks after oMPC treatment compared with pretreatment levels of HDM-specific IgE. The levels of HDM-specific IgE dropped slightly in the saline-treated control sheep at the 1 and 4 week time points compared to the pretreatment values; however this difference was not significant (FIG. 11A). A comparison between control sheep and sheep infused with different doses of oMPCs which assessed the percentage change in IgE levels in the sera from pre-treatment to 1and 4 week post treatments is shown in FIGS. 11 B & C.

Immunohistology Analysis of Lung Tissue: Inflammatory Cellular Profile in the Lungs of Asthmatic Sheep 4 Weeks after a Single Intravenous Infusion of oMPC or Saline Immunohistochemistry was performed on lung tissues sampled at autopsy from the left caudal lobe from the trial sheep. A panel of cell surface antibody markers was used on tissue sections to identify CD4, CD8, and γδ-positive T cell subsets, CD45R-positive cells, and IgE-positive cells (identifies mast cells). Eosinophils were identified as peroxidase-positive staining cells. The relative densities of these cell types were assessed in three separate lung locations comprising: the parenchyma which included non-airway tissue such as alveolar spaces and alveolar walls; the lamina propria of the airway wall which restricted the cell density analysis to the airway wall area between the luminal epithelium and the inner boundary of the airway smooth muscle bundle; and the whole airway wall which included density counts between the airway luminal epithelium and the outer adventitia bordering the alveoli.

An analysis of peroxidase-positive eosinophils on lung tissue sections sampled from asthmatic sheep indicates that the eosinophil density in the airway wall of sheep treated with 150 million oMPCs was significantly lower compared to the eosinophil density in the airway wall of saline-treated control sheep (p<0.05). Overall, these data indicate that the 150 million oMPC dose treatment given 4 weeks prior to autopsy was associated with a lower density of peroxidase-positive eosinophils in allergen exposed airway walls.

Histopathology Analysis: Eosinophil Infiltration in the Lungs of Asthmatic Sheep 4 Weeks after a Single Intravenous Infusion of oMPC or Saline and 24 Hours Following Re-Challenge with HDM Lung tissues were stained with the Luna histological method which identifies eosinophils by staining the eosinophil granules a distinctive red colour, with the background tissue staining blue.

Analysis of the findings of bronchiolar luminal debris/eosinophils and atelectasis with eosinophils in the cranial and caudal lungs did not reveal any significant differences between the control and treated animals. Analysis of the findings in the cranial and caudal lung lobes of control and treated sheep revealed a trend towards a decrease in Luna-positive eosinophils in animals in Group C (i.e. sheep treated with 150 million oMPCs). In the cranial left lung lobe, the incidence of the number of sheep showing Luna-positive eosinophils decreased from 5 in the control group to 3 sheep in the 150 million oMPC group. In the cranial right lobe, the incidence of the number of sheep showing Luna-positive eosinophils decreased from 5 sheep in the control group to 4 in the 150 million oMPC treated group. In the caudal left lung lobe, the incidence in the number of sheep with Luna-positive eosinophils decreased from 5 sheep in the control group to 3 in the 150 million oMPC treated group. In the caudal right lung lobe, the incidence in the number of sheep with Luna-positive eosinophils decreased from 4 in the control group to 2 in the 150 million oMPC treated-group. There were no differences in the incidence of sheep showing Luna-positive eosinophils between the 25 million and 75 million oMPC dose groups and the control group.

Post-hoc analyses were performed to assess whether the 150 million oMPC dose was more effective overall in reducing the presence of Luna-positive eosinophils compared to the control sheep. This analysis was performed by adding the number of sheep showing remarkable Luna-positive eosinophil staining for each of the four lung lobes examined. This analysis showed that while there were lower numbers of sheep showing Luna-positive eosinophil pathology in the 150 million oMPC group compared with the saline-treated control group.

3.3 Discussion

The present study evaluated the safety and efficacy of oMPC therapy in an ovine model of asthma. Sheep with high levels of HDM-specific IgE antibodies in their sera, compared to pre-immunization levels, were given three whole lung aerosol challenges with HDM over a 6-week period to sensitize their airways to HDM. The sheep were randomly allocated into four groups and given either saline (control), or one of three doses of oMPC treatments (25, 75, or 150 million oMPCs) by IV infusion. The sheep were then re-challenged with HDM at 7 and 28 days after their respective oMPC or saline treatments. Lung function and BAL cell analyses were assessed soon after HDM re-challenge at the time points previously indicated. IV infusion of oMPCs at 25, 75, or 150 million oMPCs was well tolerated and was without adverse events that were associated with the administration of these cells.

In the current study, the i.v. infusion of a single dose of oMPCs is associated with generally less severe physiological responses to allergen challenges compared to control sheep. For example, there was statistically significant attenuation of EAR lung function responses at four weeks after treatment with 150 million oMPCs. Interestingly, the significant reduction on EAR was delayed and observed at 4 weeks post-MPC treatment in the 150 million oMPC treatment group. Without being bound by any theory or mode of action, this delayed effect is potentially due to the long half-life of membrane bound mast cell allergen-specific IgE. This may indicate that after allergen-specific IgE is eventually shed from mast cells, MPCs are then able to reduce mast cell degranulation which ultimately results in a reduction in EAR at 4 weeks after oMPC treatment.

All three oMPC treatment groups generally have attenuated LAR lung function indices at 1 week post oMPC treatment compared to control. An analysis of pooled data from the three different doses of oMPCs shows that oMPC treatments statistically significantly improved BHR lung function indices compared to control saline-infused sheep at both the 1 week and 4 week post-treatment time points. Thus, the improvement in the BHR lung function indices for oMPC-treated sheep appeared to persist for 4 weeks after oMPC infusion. This is consistent with the interpretation of the EAR data from the 150 million dose group which indicates that significant treatment effects of oMPC infusion are apparent at the 4 week time point.

Without being bound by any theory or mode of action, the effects of oMPCs in improving lung function in sheep with experimental asthma may be related, at least in part, to the somewhat lower density of eosinophils in the airway wall in these oMPC-treated animals. The blinded morphometric analyses of the tissue densities of eosinophils in the airway wall showed that the 150 million oMPC treated group had a significantly lower density of tissue eosinophils compared with the saline-treated control sheep. Moreover, the highest oMPC dose was effective in reducing airway eosinophil density over the 4 week study period, given that all the morphometric data for the analyses were collected at autopsy four weeks after a single dose of oMPCs.

The results show that oMPC treatments are associated with lower levels of neutrophils in the BAL fluid. The mean percentage of neutrophils in total BAL cells two days after allergen challenges in all trial sheep before treatment is 0.89%. From this relatively low percentage, the 25 and 150 million oMPC treatments effectively reduced the percent neutrophils in the BAL by over 50% at the 1 week time point post oMPCs. At the later 4 week time point after oMPC administration, treatment with 75 million oMPCs significantly reduced the neutrophils in the BAL. The presence of neutrophils in the BAL fluid and airway walls has been associated with the pathology of certain phenotypes of asthma.

All sheep used in the study were selected into trial on the basis of high levels of HDM-specific IgE antibodies in their sera seven days after the completion of peripheral immunizations with HDM, and therefore only sensitized sheep were used in the study. It is noteworthy that the result shows that oMPC treatment attenuates allergen-specific IgE antibodies and that the effects last for four weeks after a single infusion of either 25 or 75 million oMPCs. In the 150 million oMPC group, the dampening of IgE was significant at 1 week post oMPC and was reduced at the four week sampling time point. Saline-treated control sheep did not show significant reductions in the levels of serum HDM-specific IgE at either the 1 or 4 week time points compared with pre-treatment values.

The invention claimed is:

1. A method of treating a respiratory condition in a human subject, the method comprising administering to the subject a population of cells enriched for STRO-1$^+$ mesenchymal precursor cells or progeny thereof.

2. The method of claim 1, wherein the respiratory condition is an acute respiratory condition or a chronic respiratory condition.

3. The method of claim 1, wherein the respiratory condition is an inflammatory respiratory condition, an obstructive respiratory condition or a restrictive respiratory condition.

4. The method of claim 3, wherein the respiratory condition is an obstructive respiratory condition or an inflammatory lung condition.

5. The method of claim 4, wherein the respiratory condition is asthma.

6. The method of claim 5, wherein the asthma is acute asthma, chronic asthma, severe asthma and/or refractory asthma.

7. The method of claim 6, wherein the asthma is long acting beta agonist (LABA) refractory asthma or steroid refractory asthma.

8. The method of claim 3, wherein the respiratory condition is a restrictive respiratory condition.

9. The method of claim 8, wherein the respiratory condition is idiopathic pulmonary fibrosis.

10. The method of claim 1, wherein the condition is allergy to house dust mite allergen (HDM).

11. The method of claim 1, wherein the population is administered systemically.

12. The method of claim 11, wherein the population is administered intravenously or intranasally.

13. The method of claim 1, wherein the population is administered a plurality of times.

14. The method of claim 1, comprising administering a further dose of the population when one or more of the following occurs:
   (i) a subject begins to persistently wheeze and/or cough and/or have chest tightness and/or have difficulty breathing;
   (ii) a subject shows one or more of the following when assessed by spirometer:
      a) 20% difference on at least three days in a week for at least two weeks;
      b) ≥20% improvement of peak flow following treatment with:
         10 minutes of inhaled β-agonist;
         six weeks of inhaled corticosteroid;
         14 days of 30 mg prednisolone.
      c) ≥20% decrease in peak flow following exposure to a trigger;
   (iii) bronchoscopy showing abnormal cells and/or foreign substances and/or blockages in the respiratory tract of a subject; or
   (iv) chest CT scan showing abnormalities of the blood vessels in the lungs, accumulation of blood or fluid in the lungs, bronchiectasis, pleural effusion or pneumonia.

15. The method of claim 1, comprising administering a dose of the population sufficient to achieve one or more of the following:
   (i) improved bronchial hyperresponsiveness;
   (ii) reduced eosinophil infiltration of the lung or bronchoalveolar lavage fluid;
   (iii) reduced neutrophil infiltration of the lung or bronchoalveolar lavage fluid;
   (iv) reduced late asthmatic response;
   (v) reduced early asthmatic response; and/or
   (vi) reduced lung remodeling/fibrosis.

16. The method of claim 1, comprising administering between $1 \times 10^6$ to $150 \times 10^6$ STRO-1$^+$ cells and/or progeny thereof.

17. The method of claim 1, wherein the population has been culture expanded prior to administration.

18. The method of claim 17 comprising administering $150 \times 10^6$ STRO-1$^+$ cells in 10 mL to the subject.

19. The method of claim 1, wherein the population is an allogenic population.

* * * * *